(12) United States Patent
Kim

(10) Patent No.: US 8,916,149 B2
(45) Date of Patent: Dec. 23, 2014

(54) PREVENTING AND TREATING SEPSIS

(75) Inventor: Minsoo Kim, Pittsford, NY (US)

(73) Assignee: University of Rochester, Rochester, NY (US)

(*) Notice: Subject to any disclaimer, the term of this patent is extended or adjusted under 35 U.S.C. 154(b) by 592 days.

(21) Appl. No.: 13/127,373

(22) PCT Filed: Nov. 3, 2009

(86) PCT No.: PCT/US2009/063125
§ 371 (c)(1),
(2), (4) Date: Aug. 4, 2011

(87) PCT Pub. No.: WO2010/062756
PCT Pub. Date: Jun. 3, 2010

(65) Prior Publication Data
US 2011/0280859 A1    Nov. 17, 2011

Related U.S. Application Data

(60) Provisional application No. 61/110,867, filed on Nov. 3, 2008.

(51) Int. Cl.
*A61K 38/48*      (2006.01)
*C12N 9/48*       (2006.01)
*C12N 9/64*       (2006.01)
*C12Q 1/37*       (2006.01)
*A61K 38/00*      (2006.01)

(52) U.S. Cl.
CPC ............... *C12N 9/6464* (2013.01); *C12Q 1/37* (2013.01); *C12Y 304/21069* (2013.01); *A61K 38/00* (2013.01); *G01N 2333/7055* (2013.01); *G01N 2333/70557* (2013.01); *G01N 2333/96461* (2013.01); *G01N 2500/02* (2013.01); *G01N 2500/04* (2013.01)
USPC ...................................... 424/94.64; 435/212

(58) Field of Classification Search
CPC ......... A61K 38/00; A61K 38/49; C12N 9/48; C12N 9/52; C12N 9/6459; C12N 15/52; C12Y 304/21; C07K 14/705; G01N 33/566
USPC .................. 424/94.64; 435/7.2, 212; 514/44; 536/23.2
See application file for complete search history.

(56) References Cited

U.S. PATENT DOCUMENTS

| | | | |
|---|---|---|---|
| 6,630,138 B2 | 10/2003 | Gerlitz et al. | |
| 6,998,122 B1* | 2/2006 | Gerlitz et al. | 424/94.64 |
| 2003/0027299 A1 | 2/2003 | Andersen et al. | |
| 2007/0155750 A1 | 7/2007 | Nouri et al. | |

FOREIGN PATENT DOCUMENTS

| | | |
|---|---|---|
| WO | WO0232461 | 4/2002 |
| WO | WO2008055145 | 5/2008 |

OTHER PUBLICATIONS

Sarangi, P.P.; Lee, H-W; Kim, M. "Activated Protein C Action in Inflammation" Brit. J. Haem., 2009 (Dec. 8), 148(6), pp. 817-833.*
Abraham et al., "Urokinase-type plasminogen activator potentiates lipopolysaccharide-induced neurtrophil activation," J. Immunol. 170:5644-51 (2003).
Abraham et al., "Drotrecogin alfa (activated ) for adults with sever sepsis and a low risk of death," N. Engl. J. Med. 353:1332-41 (2005).
Albelda et al., "Adhesion molecules and inflammatory injury," Faseb J. 8:504-12 (1994).
Aoki et al., "role of CD18-ICAM-1 in the entrapment of stimulated leukocytes in alveolar capillaries of perfused rat lungs," Am. J. Physiol. 273:H2361-71 (1997).
Bae et al., "Receptors of the protein C activation and activated protein C signaling pathways are colocalized in lipid rafts of endothelial cells," Proc. Natl. Acad. Sci. USA 104:2867-72 (2007).
Bernard et al., "Efficacy and safety of recombinant human activated protein C for severe sepsis," N. Engl. J. Med. 344:699-709 (2001).
Burns et al., "The alpha 4 beta 1 (very late antigen (VLA)-4, CD49d/CD29) and alpha 5 beta 1 (VLA-5, CD49e/CD29) integrins mediate beta 2 (CD11/CD18) integrin-independent neutrophil recruitment to endotoxin-induced lung inflammation," J. Immunol. 166:4644-9 (2001).
Cross et al., "Active immunization with a detoxified *Escheria coli* J5 lipopolysaccharide group B meningococcal outer membrane protein complex vaccine protects animals from experimental sepsis," J. Infect. Dis. 183:1079-86 (2001).
De Boer et al., "Interplay of complement and cytokines in the pathogenesis of septic shock," Immunopharmacology 24:135-48 (1992).
Dhainaut et al., "Soluble thrombomodulin, plasma-derived unactivated protein C, and recombinant human activated protein C in sepsis," Crit. Care Med. 30:S318-24 (2002).
Doerschuk et al., "CD18-dependent and -independent mechanisms of neutrophil emigration in the pulmonary and systemic microcirculation of rabbits," J. Immunol. 144:2327-33 (1990).
Doerschuk et al., "Adhesion molecules and cellular biomechanical changes in acute lung injury: Giles F. Filley Lecture," Chest 116:37S-43S (1999).

(Continued)

*Primary Examiner* — David J Steadman
*Assistant Examiner* — Paul Holland
(74) *Attorney, Agent, or Firm* — Kilpatrick Townsend & Stockton, LLP

(57) ABSTRACT

Provided are polypeptides comprising a variant activated protein C comprising one or more amino acid substitutions selected from the group consisting of K146R, D172N, C212R, K146G, R147G, R177G and combinations thereof. Also provided are nucleic acids encoding the polypeptides, and cells, compositions and kits containing the polypeptides and nucleic acids. Also provided are methods of treating sepsis in a subject comprising administering to the subject one or more of the provided polypeptides or nucleic acids. Methods of screening for polypeptides with enhanced activated protein C and for an agent for treatment of sepsis are provided. Finally, provided is a method of treating sepsis in a subject comprising administering to the subject a pharmaceutical composition comprising one or more RGD-containing peptides.

5 Claims, 17 Drawing Sheets

(56) References Cited

OTHER PUBLICATIONS

Doerschuk et al., "CD11/CD18-dependent and -independent neutrophil emigration in the lungs: how do neutrophils know which route to take?," Am. J. Respir. Cell Mol. Biol. 23:133-6 (2000).
Elphick et al., "Recombinant human activated protein C inhibits integrin-mediated neutrophil migration," Blood 113:4078-85 (2009).
Erb et al., "An RGD sequence in the P2Y(2) receptor interacts with alpha(V)beta(3) integrins and is required for G(o)-mediated signal transduction," J. Cell Biol. 153:491-501 (2001).
Feistritzer et al., "Endothelial protein C receptor-dependent inhibition of human eosinophil chemotaxis by protein C," J. Allergy Clin. Immunol. 112:375-81 (2003).
Feistritzer and Riewald, "Endothelial barrier protection by activated protein C through PAR1-dependent sphingosine 1-phosphate receptor-1 croassactivation," Blood 105:3178-84 (2005).
Finigan et al., "Activated protein C mediates novel lung endothelial barrier enhancement: role of sphingosine 1-phosphate receptor transactivation," J. Biol. Chem. 280:17286-93 (2005).
Foster et al., "The nucleotide sequence of the gene for human protein C," Proc. Natl. Acad. Sci. USA 82:4673-7 (1985).
Gale et al., "Nonenzymatic anticoagulant activity of the mutant serine protease Ser360Ala-activated protein C mediated by factor Va," Protein Sci. 6:132-40 (1997).
Gordon et al., "Quantitative fluorescence resonance energy transfer measurements using fluorescence microscopy," Biophys. J. 74:2702-13 (1998).
Gresham et al., "Ligand binding specificity of the leukocyte response integrin expressed by human neutrophils," J. Biol. Chem. 267:13895-902 (2002).
Guo et al., "Altered neutrophil trafficking during sepsis," J. Immunol. 169:307-14 (2002).
Harler et al., "Promotion of neutrophil chemotaxis through differential regulation of beta 1 and beta 2 integrins," J. Immunol. 162:6792-9 (1999).
Hellewell et al., "Disparate role of beta 2-integrin CD18 in the local accumulation of neutrophils in pulmonary and cutaneous inflammation in the rabbit," Am. J. Respir. Cell Mol. Biol. 10:391-8 (1994).
Hoffman et al., "Microcirculatory alterations in ischemia-reperfusion injury and sepsis: effects of activated protein C and thrombin inhibition," Crit. Care 9(Suppl. 4):S33-7 (2005).
Hoogenboom, "Selecting and screening recombinant antibody libraries," Nat. Biotechnol. 23:1105-16 (2005).
Kerschen et al., "Endotoxemia and sepsi mortality reduction by non-anti-coagulant-activated protein C," J. Experimental Med. 204:2439-48 (2007).
Kisiel et al., "Anticoagulant properties of bovine plasma protein C following activation by thrombin," Biochem. 16:5824-31 (1977).
Kumasaka et al., "Role of CD11/CD18 in neutrophil emigration during acute and recurrent *Pseudomonas aeruginosa*-induced pneumonia in rabbits," Am. J. Pathol. 148:1297-1305 (1996).
Liaw et al., "Identification of the protein C/activated protein C binding sites on the endothelial cell protein C receptor. Implications for a novel mode of ligand recognition by a major histocompatibility complex class 1-type receptor," J. Biol. Chem. 276:8364-70 (2001).
Lo et al., "Tumor necrosis factor mediates experimental pulmonary edema by ICAM-1 and CD18-dependent mechanisms," J. Clin. Invest 89:981-8 (1992).
Macias et al., "New insights into the protein C pathway: potential implications for the biological activities of drotrecogin alfa (activated)," Crit. Care 9(Suppl. 4):S38-45 (2005).
Mackarel et al., "Interleukin-8 and leukotriene-B(4), but not formylmethionyl leucylphenylalanine, stimulate CD18-independent migration of neutrophils across human pulmonary endothelial cells in vitro," Am. J. Respir. Cell Mol. Biol. 23:154-61 (2000).
Malik and Lo, "Vascular endothelial adhesion molecules and tissue inflammation," Pharmacol. Rev. 48:213-29 (1996).
Marlar et al., "Mechanism of action of human activated protein C, a thrombin-dependent anticoagulant enzyme," Blood 59:1067-72 (1982).

Mather et al., "The 2.8 A crystal structure of Gla-domainless activated protein C," EMBO J. 15:6822-31 (1996).
Mattern et al., "Glioma cell integrin expression and their interactions with integrin antagonists," Cancer Ther. 3A:325-40 (2005).
Menger and Vollmar, "Adhesion molecules as determinants of disease: from molecular biology to surgical research," Br. J. Surg. 83:588-601 (1996).
Mosnier et al., "Activated protein C mutant with minimal anti-coagulant activity, normal cytoprotective activity, and preservation of thrombin activable fibrinolysis inhibitor-dependent cytoprotective functions," J. Biol. Chem. 282:33022-33 (2007).
Mosnier et al., "The cytoprotective protein C pathway," Blood 109:3161-72 (2007).
Nick et al., "Recombinant human activated protein C reduces human endotoxin-induced pulmonary inflammation via inhibition of neutrophil chemotaxis," Blood 104:3878-85 (2004).
Ramamoorthy et al., "CD18 adhesion blockade decreases bacterial clearance and neutrophil recruitment after intrapulmonary *E. coli*, but not after *S. aureus*," J. Leukoc. Biol. 61:167-72 (1997).
Regan et al., "The interaction between the endothelial cell protein C receptor and protein C is dictated by the gamma-carboxyglutamic acid domain of protein C," J. Biol. Chem. 272:26279-84 (1997).
Rezaie et al., "Calcium inhibition of the activation of protein C by thrombin: role of the P3 and P3' residues," Eur. J. Biochem. 223:575-9 (1994).
Rhee et al., "Inhibition of CD1d activation suppresses septic mortality: a role for NK-T cells in septic immune dysfunction," J. Surg. Res. 115:74-81 (2003).
Richardson et al., "Charge reversal at the P3' position in protein C optimally enhances thrombin affinity and activation rate," Protein Sci. 3:711-2 (1994).
Riewald et al., "Activation of endothelial cell protease activated receptor 1 by the protein C pathway," Science 296:1880-2 (2002).
Rittirsch et al., "Functional roles for C5a receptors in sepsis," Nat. Med. 14:551-7 (2008).
Ruoslahti, "Fibronectin and its receptors," Annu. Rev. Biochem. 57:375-413 (1988).
Sessler et al., "Current concepts of sepsis and acute lung injury," Clin. Chest Med. 17:1-26 (1996).
Sixt et al., "Cell adhesion and migration properties of beta 2-integrin negative polymorphonuclear granulocytes on defined extracellular matrix molecules. Relevance for leukocyte extravasation," J. Biol. Chem. 276:18878-87 (2001).
Springer, "Traffic signals for lymphocyte recirculation and leukocyte emigration: the multi-step paradigm," Cell 76:301-14 (1994).
Sturn et al., "Expression and function of the endothelial protein C receptor in human neutrophils," Blood 102:1499-1505 (2003).
Van Deventer and Pajkrt, "Neutrophil adhesion molecules and MOF," Intensive Care Med. 23:487-8 (1997).
Vorup-Jensen et al., "Exposure of acidic residues as a danger signal for recognition of fibrinogen and other macromolecules by integrin alphaXbeta2," Proc. Natl. Acad. Sci. USA 102:1614-9 (2005).
Walker et al., "The inhibition of blood coagulation by activated protein C through the selective inactivation of activated Factor V," Biochim. Biophys. Acta 571:333-42 (1979).
Watanabe et al., "Prevention of endotoxin shock by an antibody against leukocyte integrin beta 2 through inhibiting production and action of TNF," Int. Immunol. 7:1037-46 (1995).
Wittrup, "Protein engineering by cell-surface display," Curr. Opin. Biotechnol. 12:395-9 (2001).
Xiong et al., "Crystal structure of the extracellular segment of integrin alphaVbeta3 in complex with an Arg-Gly-Asp ligand," Science 296:151-5 (2002).
Yauch et al., "Highly stoichiometric, stable, and specific association of integrin alpha3beta1 with CD151 provides a major link to phosphatidylinositol 4-kinase, and may regulate cell migration," Mol. Biol. Cell 9:2751-65 (1998).

* cited by examiner

PREVENTING AND TREATING SEPSIS

STATEMENT REGARDING FEDERALLY FUNDED RESEARCH

This invention was made with government support under Grant Nos. HL087088, HL18208, HL68571, GM065085 and GM066194 awarded by the National Institutes of Health. The government has certain rights in the invention.

CROSS-REFERENCE TO RELATED APPLICATION

This application claims priority to U.S. Provisional Application No. 61/110,867, filed Nov. 3, 2008, which is incorporated by reference herein in its entirety.

BACKGROUND

Migration of leukocytes to infection sites is vital for pathogen clearance and, thus, for host survival. Interaction of cell surface integrins with their counterpart ligands, which are expressed on the endothelial surface, results in the localization and adherence of circulating neutrophils to endothelial cells. This is followed by neutrophil activation and directed migration to sites of infection through the extracellular matrix. An important function of integrins is to concentrate neutrophils at the infection site, ensuring that their immune products and activities remain at this site, while minimizing unnecessary injury to uninfected tissues. Sustained or dysregulated integrin activation, resulting in abnormal neutrophil trafficking, as well as direct damage to the vasculature and the underlying tissue, is known to contribute to sepsis. Recombinant human activated protein C (rhAPC) is the only FDA-approved drug for treating severe sepsis. APC is a vitamin-K dependent serine protease that is derived from protein C(PC) and is well known for its anticoagulant functions.

SUMMARY

Provided are polypeptides comprising a variant activated protein C. Specifically, provided are polypeptides comprising an activated protein C (APC) polypeptide comprising one or more amino acid substitutions selected from the group consisting of K146R, D172N, C212R, K146G, R147G, R177G and combinations thereof. Also provided are nucleic acids encoding the polypeptides, and cells, compositions and kits containing the polypeptides and nucleic acids.

Provided are methods of treating sepsis in a subject comprising administering to the subject a variant activated protein C. The variant includes one or more amino acid substitutions selected from the group consisting of K146R, D172N, C212R, K146G, R147G, R177G and combinations thereof.

Methods of screening for polypeptides with enhanced activated protein C activity are provided. For example, the methods include contacting a polypeptide to be tested with a cell expressing one or both of $\beta 1$ integrin and $\beta 3$ integrin, wherein the polypeptide to be tested comprises activated protein C or a fragment thereof comprising one or more amino acid substitutions, and determining whether the polypeptide to be tested binds to the $\beta 1$ integrin or $\beta 3$ integrin better than a control activated protein C or fragment thereof. Binding better than the control indicates the polypeptide to be tested has enhanced activated protein C activity.

Also provided are methods of screening for an agent for the treatment of sepsis. The method includes contacting the agent to be screened with a cell expressing one or both of $\beta 1$ integrin and $\beta 3$ integrin, contacting an activated protein C or fragment thereof with the cell, and determining whether the agent competes with APC for binding to the $\beta 1$ integrin or $\beta 3$ integrin. If the agent competes with APC for binding, this indicates the agent is suitable for the treatment of sepsis.

Further provided is a method of treating sepsis in a subject comprising administering to the subject a pharmaceutical composition comprising one or more RGD-containing peptides.

DESCRIPTION OF DRAWINGS

FIG. 1A shows live cell images of migration of human neutrophils on fibronectin (FN)-coated cover glasses in the presence of N-formyl-Met-Leu-Phe (fMLP)±rhAPC. Cells were tracked over a 30 min period, and each line represents one cell. Experiments were repeated on neutrophil preparations from three independent donors. FIG. 1B shows directional migration of neutrophils, as measured by the under-agarose migration assay. The number of control or rhAPC-treated neutrophils migrating to fMLP (1 and 2) or to PBS (3) was counted. Representative data from three independent experiments are shown. FIG. 1C shows center-zeroed tracks of control or rhAPC-treated neutrophils migrating towards microtips containing fMLP. The scale of each graph is in μm. The speed (S, μm sec-1), migratory index (MI), and $X^D$ (mean direction in which the population is moving in degrees) are shown (mean±SEM). FIG. 1D shows migration of human neutrophils on FN coated-cover glasses in the presence of IL-8±rhAPC. FIG. 1E shows cytosolic $Ca^{2+}$ levels in stirred Fluo-4-labeled neutrophils continuously measured in a fluorometer. Control (PBS) or rhAPC treated neutrophils in $Ca^{2+}$-containing buffer were sequentially stimulated with 10 nM fMLP and 40 μM digitonin. The data are representative of at least three independent experiments.

FIG. 2A shows binding of control or 10 nM fMLP-treated neutrophils to immobilized FN in the presence of rhAPC (10 μg/ml) or Gla-less APC (10 μg/ml), or an equivalent amount of PBS. FIG. 2B shows an alignment of RGD sequences (gray) in human fibronectin (FN) (SEQ ID NO:40) and human protein C (SEQ ID NO:41). FIG. 2C shows a histogram of binding of rhAPC to human neutrophils assayed using chromogenic substrate S-2366 in the presence of 1 mM $MnCl_2$±cyclic RGD peptide (20 μg/ml), $\beta 1$ blocking Ab, $\beta 3$ blocking Ab, or $\beta 2$ blocking Ab (10 μg/ml each). *P<0.05 vs. $MnCl_2$ treated cells. FIG. 2D shows histograms of induction of ligand-induced binding site (LIBS) epitopes by rhAPC. Control (PBS) or rhAPC-treated neutrophils were incubated with the indicated concentrations of $MgCl_2$ and $CaCl_2$. The LIBS of $\beta 1$ and $\beta 3$ integrins were detected by B44 and D3 mAb, respectively. *P<0.05 vs. PBS treated cells. FIG. 2E shows histograms of solid phase binding of immobilized $\alpha 3\beta 1$, $\alpha 5\beta 1$, and $\alpha V\beta 3$ to FN or rhAPC. FIG. 2F shows a histogram of solid phase binding of immobilized $\alpha 3\beta 1$, $\alpha 5\beta 1$, and $\alpha V\beta 3$ to wild type or mutant rhAPC (RGE-APC). FIG. 2G shows migration of human neutrophils on FN coated-cover glasses in the presence of fMLP±rhPC, rhAPC, or RGE-APC. Experiments were repeated on neutrophil preparations from three independent donors. In FIGS. 2A, 2C, 2D, 2E, and 2F, results are expressed as mean±SEM of three independent experiments.

FIG. 3A shows EPCR RT-PCR on human neutrophils. Reverse transcribed cDNAs from human heart and lung served as positive controls (upper panel). FACS analysis of cell surface EPCR (lower panel). fMLP-treated cells were exposed to fMLP for 30 min prior to fixation. FIG. 3B shows histograms of binding of 10 nM fMLP-treated neutrophils to immobilized FN in the presence of rhAPC (10 µg/ml)±EPCR mAb (50 or 100 µg/ml). FIG. 3C shows a hypothetical model for rhAPC binding. Cells expressing hEPCR-mCFP and β1-mYFP exhibit FRET only when these two molecules are brought into close proximity (100 Å) after rhAPC binding. FIG. 3D shows Western blots of whole cell lysates of HEK293 cells transiently transfected with hEPCR-mCFP and β1-mYFP K562 and subjected to SDS-PAGE. FIG. 3E shows fluorescence images of transiently transfected HEK293 cells with hEPCR-mCFP and β1-mYFP demonstrating membrane localization of CFP and YFP signals. FIG. 3F shows HEK293 cells transfected with hEPCR-mCFP and β1-mYFP in delta T dish. FRET was measured by sensitized emission method and analyzed by AutoQuant software.

FIG. 4A shows a histogram of neutrophil counts in BALF from LPS treated mice. Mice were given rhAPC or RGE-APC (10 µg/mouse) or PBS 2 hours after LPS treatment. *P<0.05 between mice treated with rhAPC and PBS; n=7 per group. FIG. 4B shows survival curves for mice after CLP. 200 µg of the RGD peptide or PBS was given 12 hours before and after CLP via i.v. injection (n=20 per group). FIG. 4C shows survival curves for mice challenged with an LD90 of LPS. 200 µg of the RGD peptide or PBS was given via i.v. injection before receiving 40-39 mg/kg of LPS (i.p.) (n=10 per group). The statistical significance of mortality was determined by the Kaplan-Meyer log-rank test.

FIG. 7A shows images of increasing cycles of panning of a yeast library on HEK293 cells. FIG. 7B shows a histogram of recovery percentage for increasing cycles of panning of a yeast library on HEK293 cells.

DETAILED DESCRIPTION

Figure 1A:
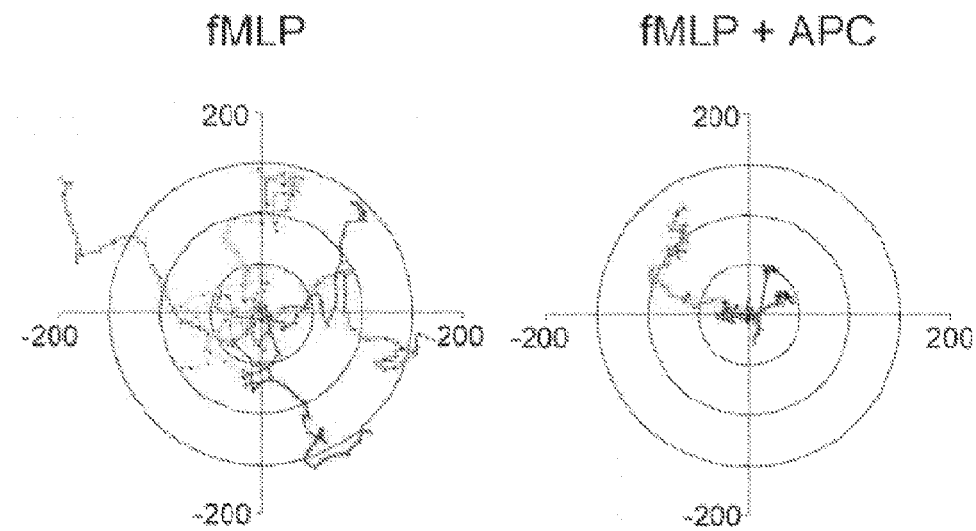
FIGS. 1A-1E show recombinant human activated protein C (rhAPC) inhibits neutrophil migration.

During inflammation, tissue injury results from excessive infiltration and sequestration of activated leukocytes. Recombinant human activated protein C (rhAPC) has been shown to protect patients with severe sepsis, although this protective effect remains unclear. As described herein, rhAPC was demonstrated to directly bind to β1 and β3 integrins and to inhibit neutrophil migration, both in vitro and in vivo. It was found that human APC possesses an Arg-Gly-Asp (RGD) sequence, which is critical for the inhibition. Mutation of this sequence abolished both integrin binding and inhibition of neutrophil migration. In addition, an RGD peptide enhanced the survival of septic mice. Thus, leukocyte integrins are cellular receptors for rhAPC, and their interaction decreases neutrophil recruitment into tissues, providing a mechanism by which rhAPC protects from sepsis.

Provided herein are variant APC polypeptides and variant APC polypeptide fragments. Such variants contain a RGD motif and are selected for their ability to bind integrins, such as β1 and/or β3 integrins. Optionally, the variant APC polypeptides bind with higher affinity to the integrins than wild-type APC. Specifically, provided are APC polypeptides comprising one or more amino acid substitutions. There are a variety of sequences that are disclosed on Genbank, at www.pubmed.gov and these sequences are herein incorporated by reference in their entireties as are individual subsequences or fragments contained therein. For example, the amino acid sequence of human protein C can be found at GenBank Accession No. NP_000303.1 and P04070. Human protein C (SEQ ID NO:2) is synthesized as a single chain precursor, which is cleaved into a light chain and a heavy chain held together by a disulfide bond. Activated protein C is shown as SEQ ID NO:1. Thus, provided are polypeptides of an APC comprising one or more amino acid substitutions selected from the group consisting of K146R, D172N, C212R, K146G, R147G, R177G and combinations thereof. Optionally, the APC comprises the amino acid substitution K146R or D172N. Optionally, the APC comprises the amino acid substitutions K146G and R147G. Optionally, the APC comprises the amino acid substitutions R177G, K146G and R147G. Optionally, the APC comprises the amino acid substitutions C212R, K146G and R147G. Optionally, the APC comprises the amino acid substitutions C212R and R177G. Optionally, the APC further comprises the amino acid substitutions KKK191-193AAA and/or RR229/230AA.

Optionally, the APC comprises SEQ ID NO:1. Thus, provided are polypeptides of SEQ ID NO:1 with one or more amino acid substitutions. The amino acid substitutions include K146R, D172N, C212R, K146G, R147G, R177G and combinations thereof. Optionally, the polypeptides further include amino acid substitutions RR229/230AA and/or KKK191-193AA. Thus, provided are polypeptides comprising SEQ ID NOs:3-32, 42 and 43.

As used herein, the terms peptide, polypeptide, protein or peptide portion are used broadly herein to mean two or more amino acids linked by a peptide bond. The term fragment is used herein to refer to a portion of a full-length polypeptide or protein. It should be recognized that the term polypeptide is not used herein to suggest a particular size or number of amino acids comprising the molecule and that a peptide of the invention can contain up to several amino acid residues or more.

A polypeptide comprising a fragment of the variant APC polypeptides are provided. Thus, provided are fragments of SEQ ID NO:1 comprising one or more amino acid substitutions. Thus, the fragments include one or more of the amino acid substitutions selected from K146R, D172N, C212R, K146G, R147G, R177G and combinations thereof. Optionally, the fragments further include amino acid substitutions RR229/230AA and/or KKK191-193AA. The fragments also include an RGD motif. It is understood that the term fragment includes a functional fragment. A functional fragment of a variant APC is selected for its ability to bind integrins, such as β1 and/or β3 integrins, for example, as shown in the Examples.

As discussed above, the polypeptides provided herein, including fragments, have a desired function. The polypeptides as described herein selectively bind β1 and/or β3 integrins. By binding is meant a detectable binding of at least about 1.5 times the background of the assay method. For selective or specific binding such a detectable binding can be detected for a given agent but not a control antigen or agent. Optionally, the polypeptides described herein bind with similar or higher affinity than wild-type APC (i.e., SEQ ID NO:1). By binding with higher affinity is meant a detectable binding at least about 1.5 times higher than the binding affinity of a control (e.g., wild type) for a particular assay method. The polypeptides are tested for their desired activity using the in vitro assays described herein, or by analogous methods, after which their therapeutic, diagnostic or other purification activities are tested according to known testing methods.

As with all peptides, polypeptides, and proteins, including fragments thereof, it is understood that additional modifications in the amino acid sequence of the variant APC polypeptides can occur that do not alter the nature or function of the peptides, polypeptides, or proteins. Such modifications include conservative amino acid substitutions and are discussed in greater detail below.

The polypeptides described herein can be further modified so long as the desired function is maintained. It is understood that one way to define any known modifications and derivatives or those that might arise, of the disclosed genes and proteins herein is through defining the modifications and derivatives in terms of identity to specific known sequences. Specifically disclosed are polypeptides which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the APC and APC variants provided herein. For example, provided are polypeptides which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to one of SEQ ID NOs:3-32. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman Adv. Appl. Math. 2: 482 (1981), by the identity alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Protein modifications include amino acid sequence modifications. Modifications in amino acid sequence may arise naturally as allelic variations (e.g., due to genetic polymorphism) or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations. Post-translational modifications can include variations in the type or amount of carbohydrate moieties of the protein core or any fragment or derivative thereof. Amino acid sequence modifications typically fall into one or more of three classes: substitutional, insertional or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 1 and are referred to as conservative substitutions.

TABLE 1

Amino Acid Substitutions

| Amino Acid | Substitutions (others are known in the art) |
| --- | --- |
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods including the methods described in the Examples below. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Nucleic acids that encode the aforementioned variant polypeptide sequences and fragments thereof are also disclosed. Thus, provided is a nucleic acid sequence encoding an APC comprising one or more amino acid substitutions selected from the group consisting of K146R, D172N, C212R, K146G, R147G, R177G. and combinations thereof. Optionally, the encoded APC comprises the amino acid substitutions K146R or D172N. Optionally, the encoded APC comprises the amino acid substitutions K146G and R147G. Optionally, the encoded APC comprises the amino acid substitutions R177G, K146G and R147G. Optionally, the encoded APC comprises the amino acid substitutions C212R, K146G and R147G. Optionally, the encoded APC comprises the amino acid substitutions C212R and R177G. Optionally, the encoded APC comprises an RGD motif. Optionally, the encoded APC further comprises the amino acid substitutions KKK191-193AAA and/or RR229/230AA. Thus, provided are nucleic acids encoding SEQ ID NOs:1-32, 42 and 43. These nucleic acid sequences include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Isolated nucleic acid molecules can be produced by standard techniques. For example, polymerase chain reaction (PCR) techniques can be used to obtain an isolated nucleic acid containing a nucleotide sequence described herein. Various PCR methods are described, for example, in PCR Primer: A Laboratory Manual, Dieffenbach and Dveksler, eds., Cold Spring Harbor Laboratory Press, 1995. Various PCR strategies also are available by which the site-specific nucleotide sequence modifications described herein can be introduced into a template nucleic acid. Optionally, isolated nucleic acids are chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids disclosed herein also can be obtained by mutagenesis of, e.g., a naturally occurring DNA.

Also provided are expression vectors comprising the disclosed nucleic acids, wherein the nucleic acids are operably linked to an expression control sequence. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Preferred promoters controlling transcription from vectors in mammalian host cells may be obtained from various sources, for example, the genomes of viruses such as polyoma, Simian Virus 40 (SV40), adenovirus, retroviruses, hepatitis B virus and most preferably cytomegalovirus, or from heterologous mammalian promoters, e.g. beta actin promoter or EF1 promoter, or from hybrid or chimeric promoters (e.g., cytomegalovirus promoter fused to the beta actin promoter). The early and late promoters of the SV40 virus are conveniently obtained as an SV40 restriction fragment which also contains the SV40 viral origin of replication. The immediate early promoter of the human cytomegalovirus is conveniently obtained as a HindIII E restriction fragment. Of course, promoters from the host cell or related species also are useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers usually function to increase transcription from nearby promoters. Enhancers can also contain response elements that mediate the regulation of transcription. While many enhancer sequences are now known from mammalian genes (globin, elastase, albumin, fetoprotein and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

Optionally, the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter. Other preferred promoters are SV40 promoters, cytomegalovirus (plus a linked intron sequence), beta-actin, elongation factor-1 (EF-1) and retroviral vector LTR.

The vectors also can include, for example, origins of replication, scaffold attachment regions (SARs), and/or markers. A marker gene can confer a selectable phenotype, e.g., antibiotic resistance, on a cell. This marker product is used to determine if the gene has been delivered to the cell and once delivered is being expressed. Examples of marker genes include the E. coli lacZ gene, which encodes β galactosidase, green fluorescent protein (GFP), and luciferase. Examples of suitable selectable markers for mammalian cells are dihydrofolate reductase (DHFR), thymidine kinase, neomycin, neomycin analog G418, hygromycin, and puromycin. When such selectable markers are successfully transferred into a mammalian host cell, the transformed mammalian host cell can survive if placed under selective pressure. In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

Further provided are cultured cells comprising the expression vectors. Such expression vectors and cultured cells can be used to make the provided polypeptides. Thus, the expression vectors disclosed herein containing the above described nucleic acid sequences can be used, for example, to transfect or transduce either prokaryotic (e.g., bacterial) cells or eukaryotic cells (e.g., yeast, insect, or mammalian) cells. Such cells can then be used, for example, for large or small scale in vitro production of the provided variant APC polypeptides and fragments thereof. Such methods involve culturing the cells under conditions for production of the polypeptides and isolating the polypeptides from the cells or from the culture medium.

Provided herein are compositions containing the provided polypeptides or nucleic acids and a pharmaceutically acceptable carrier. The herein provided compositions are administered in vitro or in vivo. By pharmaceutically acceptable carrier is meant a material that is not biologically or otherwise undesirable, i.e., the material is administered to a subject, e.g., with a variant APC, without causing any undesirable biological effects or interacting in a deleterious manner with any of the other components of the pharmaceutical composition in which it is contained. The carrier is selected to minimize any degradation of the active ingredient and to minimize any adverse side effects in the subject.

Suitable carriers and their formulations are described in *Remington: The Science and Practice of Pharmacy*, $21^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained release preparations such as semipermeable matrices of solid hydrophobic polymers containing the immunogenic polypeptides. Matrices are in the form of shaped articles, e.g., films, liposomes or microparticles. Certain carriers may be more preferable depending upon, for instance, the route of administration and concentration of composition being administered. Carriers are those suitable for administration of the agent, e.g., the variant APC polypeptide, to humans or other subjects.

The compositions are administered via any of several routes of administration, including, for example, topically, orally, parenterally, intravenously, intraperitoneally, intramuscularly, subcutaneously, intracavity, transdermally, intrahepatically, intracranially, nebulization/inhalation, or by instillation via bronchoscopy.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, antioxidants, chelating agents, and inert gases and the like.

Optionally, the composition is administered by oral inhalation, nasal inhalation or intranasal mucosal administration. As used herein, these terms mean delivery of the compositions into the nose and nasal passages through one or both of the nares and can comprise delivery by a spraying mechanism or droplet mechanism, or through aerosolization of the nucleic acid or vector. Administration of the compositions by inhalant is through the nose or mouth via delivery by a spraying or droplet mechanism. For example, in the form of an aerosol. Delivery is optionally directly to any area of the respiratory system (e.g., lungs) via intubation.

Formulations for topical administration include ointments, lotions, creams, gels, drops, suppositories, sprays, liquids and powders. Conventional pharmaceutical carriers, aqueous, powder or oily bases, thickeners and the like are optionally necessary or desirable.

Compositions for oral administration include powders or granules, suspensions or solutions in water or non-aqueous media, capsules, sachets, or tablets. Thickeners, flavorings, diluents, emulsifiers, dispersing aids or binders are optionally desirable.

Provided herein are methods of treating sepsis in a subject. Such methods include administering one or more of the provided nucleic acids, one or more of the provided polypeptides, and combinations thereof to the subject. Optionally, the nucleic acids and/or polypeptides are contained within a pharmaceutical composition as described above.

Optionally, the nucleic acid is administered by a vector comprising the nucleic acid. There are a number of compositions and methods which can be used to deliver nucleic acids to cells, either in vitro or in vivo via, for example, expression vectors. These methods and compositions can largely be broken down into two classes: viral based delivery systems and non-viral based delivery systems. Such methods are well known in the art and readily adaptable for use with the compositions and methods described herein.

As used herein, plasmid or viral vectors are agents that transport the disclosed nucleic acids into the cell without degradation and include a promoter yielding expression of the gene in the cells into which it is delivered. Viral vectors are, for example, Adenovirus, Adeno-associated virus, Herpes virus, Vaccinia virus, Polio virus, Sindbis and other RNA viruses, including these viruses with the HIV backbone. Also preferred are any viral families which share the properties of these viruses which make them suitable for use as vectors. Retroviral vectors, in general, are described by Verma, I. M., Retroviral vectors for gene transfer. In Microbiology-1985, American Society for Microbiology, pp. 229-232, Washington, (1985), which is incorporated by reference herein for the vectors and methods of making them. The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang et al., BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency after direct, in vivo delivery to airway epithelium, hepatocytes, vascular endothelium, CNS parenchyma and a number of other tissue sites. Other useful systems include, for example, replicating and host-restricted non-replicating vaccinia virus vectors.

The provided polypeptides or nucleic acids can be delivered via virus like particles. Virus like particles (VLPs) consist of viral protein(s) derived from the structural proteins of a virus. Methods for making and using virus like particles are described in, for example, Garcea and Gissmann, *Current Opinion in Biotechnology* 15:513-7 (2004).

The provided polypeptides can be delivered by subviral dense bodies (DB). DBs transport proteins into target cells by membrane fusion. Methods for making and using DBs are described in, for example, Pepperl-Klindworth et al., *Gene Therapy* 10(3):278-84 (2003).

The provided polypeptides can be delivered by tegument aggregates. Methods for making and using tegument aggregates are described in International Publication NO. WO 2006/110728.

Optionally, the pharmaceutical composition comprises an effective amount or effective dosage of the provided polypeptides or nucleic acids. An effective amount of the pharmaceutical composition comprises a dosage between about 0.01 mg per kg body weight of the subject up to about 100 mg per kg body weight of the subject. The dosage can be, for example, from about 0.01, 0.025, 0.05, 0.1, 0.5 to about 25, 50, 75, or 100 mg/kg. Optionally, the pharmaceutical composition is administered from 0.01 to 50 µg/kg/hr. Optionally, the pharmaceutical composition is administered from 0.1 to 25 µg/kg/hr. Optionally, the pharmaceutical composition is administered as an intravenous infusion. Optionally, 2.5 to 25 mg of the pharmaceutical composition is administered as an intravenous infusion. Doses are administered in one or more dose administrations daily, for one or several days.

Also provided herein is a method of treating sepsis in a subject comprising administering to the subject one or more RGD-containing peptides. Optionally, the RGD-containing peptide is a cyclic RGD-containing peptide. Optionally, the RGD-containing peptide is selected from the group consisting of c[RGDD(tert-butylglycine)(m-aminomethylbenzoic acid)]; c[(3-mercaptopropionic acid)RGDD(tert-butylglycine)C]—NH$_2$; G-c[(penicillamine)RARGDNPC]-A; acetyl-c[(penicillamine)-O-methyltyrosine-ARGDN(tetrahydroisoquinoline-3-carboxylic acid)C]—NH$_2$, and acetylphenylalanine-c[CRGDTFC]—NH$_2$. Optionally, the RGD-containing peptide is acetyl-c[(penicillamine)-O-methyltyrosine-ARGDN(tetrahydroisoquinoline-3-carboxylic acid)C]—NH$_2$. The RGD containing peptides can be formulated in a pharmaceutical composition as described above.

The methods optionally include administering one or more other therapeutic or prophylactic regimens. Thus, the provided methods can further comprise the step of administering a second therapeutic agent to the subject. The second therapeutic agent is, optionally, drotrecogin alfa (activated) (Xigris®, Eli Lilly, Indianapolis, Ind.). Optionally, the second therapeutic agent is SEQ ID NO:1. Optionally, the second therapeutic agent is an RGD-containing peptide. As used throughout, a therapeutic agent is a compound or composition effective in ameliorating a pathological condition. Illustrative examples of other therapeutic agents include, but are not limited to, antibiotics, anti-inflammatory agents, vasopressors, pain killers, and sedatives. Optionally, the anti-inflammatory agent is a corticosteroid. Optionally, the therapeutic agent is an antibody that blocks β1 or β3 integrin activity.

Anti-inflammatory agents, that may be administered in combination with the provided compositions include, but are not limited to steroids, cyclosporine, cyclosporine analogs, cyclophosphamide methylprednisone, prednisone, azathioprine, FK-506 (Fujisawa Pharmaceuticals, Deerfield, Ill.), 15 deoxyspergualin, and other immunosuppressive agents that act by suppressing the function of responding immune cells (including, for example, T cells), directly (e.g., by acting on the immune cell) or indirectly (by acting on other mediating cells). Immunosuppresive agents also include, ORTHOCLONE® (OKT3) (Ortho Biotech, Raritan, N.J.), SANDIMMUNE® ORAL (cyclosporine) (Sandoz Pharmaceuticals, Hanover, N.J.), PROGRAF® (tacrolimus) (Fujisawa Pharmaceuticals, Deerfield, Ill.), CELLCEPT® (mycophenolate) (Roche Pharmaceuticals, Nutley, N.J.), azathioprine, glucorticosteroids, and RAPAMUNE® (sirolimus) (Wyeth, Collegeville, Pa.).

Any of the aforementioned second therapeutic agents or treatment regimes can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to either concomitant, simultaneous, or sequential administration of two or more agents.

The terms effective amount and effective dosage are used interchangeably. The term effective amount is defined as any amount necessary to produce a desired physiologic response. Effective amounts and schedules for administering the compositions are determined empirically. The dosage ranges for the administration of the compositions are those large enough to produce the desired effect in which the symptoms or disorder are affected. The dosage is not so large as to cause substantial adverse side effects, such as unwanted cross-reactions, anaphylactic reactions, and the like. Generally, the dosage varies with the age, condition, sex, type of disease and extent of the disease in the patient, route of administration, or whether other drugs are included in the regimen, and is determined by one of skill in the art. The dosage is optionally adjusted by the individual physician in the event of any contraindications.

Also provided are methods of screening for polypeptides with enhanced APC activity. The method includes contacting a polypeptide to be tested with a cell expressing one or both of β1 integrin and β3 integrin, wherein the polypeptide to be tested comprises APC or a fragment thereof comprising one or more amino acid substitutions, and determining whether the polypeptide to be tested binds to the β1 integrin or β3 integrin better than a control APC or fragment thereof, wherein binding better than the control indicates the polypeptide to be tested has enhanced APC activity. Optionally, the contacting step includes contacting a cell expressing the polypeptide to be tested with the cell expressing one or both of β1 integrin and β3 integrin. Optionally, the polypeptide to be tested is made by mutagenizing APC or a fragment thereof using, e.g., error-prone PCR. Optionally, the control APC comprises SEQ ID NO:1.

Also provided is a method of screening for an agent for treatment of sepsis including contacting the agent to be screened with a cell expressing one or both of β1 integrin and β3 integrin, contacting an APC or fragment thereof with the cell, and determining whether the agent competes with APC for binding to the β1 integrin or β3 integrin. If the agent competes with APC for binding, this indicates the agent is suitable for treatment of sepsis. Optionally, the APC comprises SEQ ID NO:1. Optionally, the APC or fragment thereof comprises an RGD motif.

The polypeptide, nucleic acids, compositions and combinations thereof described herein can be assembled in kits. Thus, provided are kits comprising one or more of the provided nucleic acids and a container. Also provided are kits comprising one or more of the provided polypeptides and a container. Suitable containers include vials, packets, or intravenous bags. Optionally, the kit includes measured amounts of a pharmaceutically acceptable composition comprising the nucleic acid or polypeptide. The kit can also include instruments useful in administration, such as needles, syringes, tubing, catheters, bandages, and tape. The kits can also include instructions for use.

As used throughout, by a subject is meant an individual. Thus, the subject can include, for example, domesticated animals, such as cats and dogs, livestock (e.g., cattle, horses, pigs, sheep, and goats), laboratory animals (e.g., mice, rabbits, rats, and guinea pigs), mammals, non-human mammals, primates, non-human primates, rodents, birds, reptiles, amphibians, fish, and any other animal. The subject can be a mammal such as a primate or a human. The term subject also includes individuals of different ages. Thus, a subject includes an infant, child, teenager or adult.

As used herein the terms treatment, treat or treating refers to a method of reducing the effects of a disease or condition or symptom of the disease or condition. Thus in the disclosed method, treatment can refer to a 5%, 10%, 20%, 30%, 40%, 50%, 60%, 70%, 80%, 90% or 100% reduction in the severity of an established disease or condition or symptom of the disease or condition. For example, a method for treating a disease is considered to be a treatment if there is a 5% reduction in one or more symptoms of the disease in a subject as compared to control. Thus the reduction can be a 5, 10, 20, 30, 40, 50, 60, 70, 80, 90, 100% or any percent reduction in between 10 and 100 as compared to native or control levels. It is understood that treatment does not necessarily refer to a cure or complete ablation of the disease, condition or symptoms of the disease or condition.

As used herein, the terms prevent, preventing and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 5, 10, 20, 30, 40, 50, 60, 70, 80, 90 percent or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a substitution or modification is disclosed and discussed and a number of other substitutions or modifications that can be made, each and every combination and permutation can be combined, and the modifications that are possible are specifically contemplated unless specifically indicated to the contrary. Likewise, any subset or combination of these is also specifically contemplated and disclosed. This concept applies to all aspects of this disclosure including, but not limited to, steps in methods of using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

EXAMPLES

Example 1

Direct Binding of Activated Protein C to Integrins and its Protective Effects in Sepsis Materials and Methods Reagents. Recombinant Human APC (rhAPC) was obtained from Eli Lilly (Indianapolis, Ind.). The protein C mutant containing Glu substitutions in place of Asp-222 (D222E) was constructed by overlap extension PCR. The inner complementary primers were 5'-GACCAGGCGGG-GAGAGAGCCCCTGGCAGGTG-3' (SEQ ID NO:33) and 5'-CACCTGCCAGGGGCTCTCTCCCCGCCTGGTC-3' (SEQ ID NO:34). The outer primers corresponded to vector plasmid cDNA (pRC/CMV) bases 837 to 856 and 1038 to 1065. The second round PCR product was digested with HindIII and XbaI, and inserted into pcDNA 3.1(+)/Hygro vector (Invitrogen, Carlsbad, Calif.). The mutant zymogen was expressed in HEK293 cells, purified and converted to activated protein C by thrombin, and separated from thrombin by an FPLC Mono Q column as described (Bae et al., Proc Natl Acad Sci USA 104:2867 (2007)).

DNA Plasmids and Constructs. For hEPCR-mCFP, PCR extensions were performed on wild type hEPCR cDNA in pSVzeo as a template. The upstream primer 5'-ATATAAAGCTTGCCACCATGTTGACAA-CATTGCTGCC-3' (SEQ ID NO:35) with a HindIII site and the downstream primer 5'-TATATACCGGTCCACATCGC-CGTCCACCTGTGC-3' (SEQ ID NO:36) with a AgeI site were used with hEPCR-pSVzeo. After digestion with HindIII and AgeI, the PCR fragment was inserted into HindIII and AgeI digested pECFP.

For β1-mYFP with 5 amino acid residue linker, PCR extension was performed using wild type β1 subunit cDNA (Genbank Accession No. BC020057) as a template with the upstream primer 5'-ATATACTCGAGGCCACCATGAATT-TACAACCAATTTT-3' (SEQ ID NO:37) containing XhoI site and the downstream primer 5'-TATATACCGGTC-CTTTTCCCTCATACTTCGGAT-3' (SEQ ID NO:38) containing AgeI site. After digestion with XhoI and AgeI, PCR product and mYFP then ligated to generate β1(5)-mYFP containing 5 amino acid residue linker of GPVAT. Monomeric mCFP and mYFP mutants were generated by replacing Leu-221 at the crystallographic dimer interface with a Lys.

Human Neutrophil Preparation.

Blood was collected from healthy volunteers via antecubital vein puncture in heparin or EDTA-containing vacutainers. Granulocytes and erythrocytes were separated from whole blood by centrifugation through a Histopaque 1077 (Sigma, St. Louis, Mo.) density gradient. The cell suspension containing neutrophils was collected and washed with HBSS−/− (without calcium or magnesium) at 1250 rpm for 10 min at 4° C. Remaining erythrocytes were removed by hypotonic lysis, yielding a neutrophil purity of greater than 98%. Neutrophils were resuspended in cold HBSS−/− for experimentation.

Under-Agarose Migration Assay.

Delta T dishes (Bioptechs, Butler, Pa.) were coated with fibronectin (FN). Plates were then rinsed with the appropriate media and allowed to air-dry. Molten agarose (Seakem GTG, FMC Bioproducts, Rockland, Me.) was prepared as described (Harler et al., J Immunol., 162:6792 (1999)). Two milliliters of the resulting gel was added to each dish and allowed to solidify at 4° C. for 5 min. Three wells that were 2 mm apart were prepared in the agarose using a template and a beveled punch that was coated with polymixin B. Care was taken to ensure that the plate bottom was not scratched. Punch sections were removed with an aspirator, and the gel was then equilibrated for one hour at 37° C. The wells were then aspirated and loaded with 30 ml of one of the following: PBS (left well), a suspension containing approximately 200,000 cells (middle well), or a solution containing 5 pmol of fMLP (right well). A subset of cells was treated with 10 µg/ml rhAPC at 37° C. for 20 min prior to being loaded into the wells. The dishes were incubated for 60 min at 37° C., and then fixed with 10% buffered formalin. Counts were then made of the number of cells that had migrated 1 mm towards the right well (towards fMLP, directional migration), 0.5 mm towards the left and right wells ("straddle"), and 1 mm towards the left well (random migration). The experiments were repeated three times per condition.

Measurement of Random Migration and Micropipette Assay.

Delta T dishes were coated with human FN (50 µg/ml, BD Biosciences, San Jose, Calif.) for overnight at 4° C. and then for 4 h at room temperature. Plates were then rinsed with L-15 media. Human neutrophils (approximately 500,000) were incubated, in the presence or absence of 10 µg/ml of wild type rhAPC or mutant RGE-APC in 500 µL-15 media containing 2 mg/ml glucose for 20 min at 37° C. The cells were then added to FN-coated dishes in 1.5 ml of L-15 with 2 mg/ml of glucose. For neutrophil live cell staining, 2 µM Green Cell Tracker CMFDA (5-chloromethylfluorescein diacetate; Molecular Probes, Carlsbad, Calif.) was used. Temperature was maintained at 37° C. throughout the experiment using a FCS2 live-cell imaging chamber (Bioptechs, Butler, Pa.). Images were acquired for 30 to 60 minutes under a 10× objective lens using a Nikon TE-2000U inverted microscope. Phase contrast images were acquired every 5 seconds and fluorescence images every 30 seconds. Cell paths were traced using MetaVue™ imaging software (Molecular Devices Corporation, Downingtown, Pa.).

Random migration was investigated by adding fMLP or IL-8 to media at a final concentration of $10^{-8}$M and analyzed by manually tracing the outline of each cell in selected frames (i.e., at 50 second intervals). The x and y coordinates of each cell were measured using ImageJ software and were corrected so that the starting position was x=0 and y=0.

Directional migration was investigated using a micropipette assay to analyze the dynamics of neutrophil migration on different integrin ligands. Sterile Femtotips II micropipette tips (Eppendorf, Westbury, N.Y.) were loaded with 5 µl of 1 µM fMLP and then placed on the bottom of FN-coated delta T dishes that had been pre-warmed to 37° C. Image acquisition began within 2 minutes of tip placement.

The time-lapsed images of migrating neutrophils were taken under phase contrast microscopy. Each image was thresholded and binarized based on brightness to define the centroids of the neutrophils. The closest centroids between consecutive images were linked as a trajectory under the assumption that these centroids were made by the same neutrophil. The maximum distance between the closest centroids was also defined to preclude the artifacts due to cells moving into and out of the field of view. To demonstrate the randomness of chemokinesis and the distances that each cell travel, the starting points of the trajectories of the neutrophils were translated to the origin.

FACS Analysis.

Neutrophils were pretreated with 10 µg/ml of rhAPC in HBS (20 mM Hepes, pH7.5, 140 mM NaCl)+1 mM $Ca^{2+}$ and 1 mM $Mg^{2+}$, or +3 mM $Ca^{2+}$ and 0.6 mM $Mg^{2+}$ for 30 min at 37° C. LIBS mAbs (B44 and D3) were added 5 minutes prior to fixation with 3.7% formaldehyde for 10 minutes at room temperature. Then cells were washed and incubated with PE-labeled goat anti-mouse IgG for 30 minutes at 4° C. in the dark. Cells were then washed and resuspended in PBS for FACS analysis.

Neutrophil Adhesion Assays.

The adhesion assay was carried out essentially as described (Vorup-Jensen et al., PNAS 102:1614 (2005)). Cover slips were coated with FN in coating buffer (150 mM NaCl/20 mM Tris.HCl, pH 9.0) for over night at 4° C. and for 4 hours at room temperature. Residual binding sites were blocked by incubation of the wells with 0.05% (wt/vol) polyvinylpyrrolidone in PBS for 30 minutes at room temperature. $2.5 \times 10^5$/ 250 µl of neutrophils were suspended in L15 medium plus 2 mg/ml glucose and pretreated for 15 minutes at 37° C. with 10 µg/ml rhAPC, 50 µg/ml human EPCR blocking mAb (RCR-252), or 10 µg/ml Gla-less rhAPC (Enzyme Research Lab., IN). The cover slips were aspirated, and washed with L15 medium. 250 µl of L15/2 mg/ml glucose medium containing 10 µg/ml rhAPC, 50 µg/ml human EPCR blocking mAb, or 10 µg/ml Gla-less rhAPC, with/without 20 nM fMLP was placed on each cover slip and prewarmed for 15 minutes at 37° C. Cells (250 µl) were then immediately added, and further incubated at 37° C. for 15 minutes. Unbound cells were then washed with warm L15 medium. The bound cells were then fixed with formaldehyde. For each experimental condition from three independent donors, five random phase-contrast images were obtained, and the number of cells in each well was scored from printed micrographs.

Integrin Ligand Binding Assay.

The solid phase binding assay was performed using purified soluble human $\alpha 3\beta 1$, $\alpha 5\beta 1$, and $\alpha V\beta 3$ (US Biological, Swampscott, Mass.). Two (2) µg/ml of soluble integrins were added to microtiter wells for capture with immobilized monoclonal antibody against $\beta 1$ or $\beta 3$ subunits (mAb TS2/6 for $\beta 1$ and mAb BB10 (Chemicon, Temecula, Calif.) for $\beta 3$ integrins). 10 µg/ml rhAPC, 10 µg/ml RGE-APC, or 5 µg/ml of human FN was incubated in the presence of 1 mM $Ca^{2+}$ and $Mg^{2+}$ plus 1 mM $Mn^{2+}$ for 1 h at room temperature. After washing, bound APC was chromogenically detected by peroxidase-streptavidin conjugate anti-PC (Diapharma, West Chester, Ohio) or chromogenic substrate S-2366 (Diapharma, West Chester, Ohio). To minimize dissociation, all wash buffers contained 1 mM $Mn^{2+}$, and <15 minutes elapsed between the end of binding and beginning of color development. Functional blocking antibodies for integrins were from Chemicon (Temecula, Calif.).

Intracellular $Ca^{2+}$ Measurement.

$1 \times 10^7$ cells/ml of human neutrophils were labeled with 504 Fluo-4 AM (Molecular Probes, Eugene, Oreg.) at 37° C. for 30 minutes, then at room temperature for an additional 5 to 10 minutes. After washing twice, cells were resuspended to $4 \times 10^6$ cells/ml (6 ml) in F15 and incubated at RT for de-esterification. For measurements, cells ($4 \times 10^6$) were spun down in a microtube (1 ml), resuspend in 1 ml of F15 at 37° C., transferred to a quartz cuvette containing a fluorometric stir bar and 1 ml of the same buffer at 37° C., and fluorescence signals were measured in the fluorometer.

FRET.

Dynamic FRET imaging was carried out using a Nikon Eclipse TE2000-U microscope (Nikon, Melville, N.Y.) equipped with a Dual-View (Optical Insights, Tucson, Ariz.) and CFP/YFP dual-band filter set (Chroma, Rockingham, Vt.). TIRF imaging was performed with a white light TIRF aperture diaphragm and a 100×TIRF 1.49 NA oil immersion objective coupled to a QuantEM EMCCD (Roper Scientific, Tucson, Ariz.). The microscope was controlled by NIS element software (Nikon, Melville, N.Y.) and data analysis was performed with AutoDeblur (Autoquant Imaging, Troy, N.Y.) by the sensitized emission method (Gordon et al., Biophys. J. 74:2702 (1998)). 48 hours after co-transfection with hEPCR-mCFP and β1-mYFP DNA construct in Delta T dish (Fisher Scientific, Pittsburgh, Pa.), HEK293 cells were washed with PBS and then 1 ml L15 medium supplemented with 2 mg/ml D-glucose. Cells were equilibrated for about 10 minutes at 37° C. in a FCS2 live cell imaging chamber (Bioptechs, Butler, Pa.). Then each image of CFP, YFP, and bright field of cells was taken for 0.1 second for hEPCR-mCFP and 1 second for β1-mYFP with 2×2 binning through a 100× oil immersion objective lens every 10 seconds for 15 minutes.

Neutrophil Recruitment into Airspace.

Mice (C57BL/6, 6-8 weeks) were anesthetized with avertin and then intranasally administered 30 μg of LPS (Sigma-Aldrich, St. Louis, Mo.). Two hours later the mice were tail vain injected with rhAPC or RGE-APC (10 μg/mouse) or PBS. Mice were sacrificed 4 hours later and bronchioalveolar lavage was harvested. Cells were fixed with 4% formaldehyde for 20 minutes. Cells were counted using microbeads (Polyscience, Niles, Ill.) by flow cytometry. Cells were stained with Gr-1 APC antibody (eBioscience, San Diego, Calif.) and collected by flow cytometry. Data were analyzed using FlowJo software (Tree Star, Ashland, Oreg.).

Induction of Sepsis by Cecal Ligation and Puncture (CLP).

CLP was used to induce acute septic peritonitis as described (Rhee et al., J Surg Res 115:74 (2003)). Briefly, mice (C57BL/6, 6-8 weeks) were anesthetized using inhaled Isoflurane, a midline incision (approximately 1 cm) was made below the diaphragm, the cecum was excised to the surface, ligated approximately 4 cm distal and then punctured through and through with a 22-gauge needle. Cecum was gently squeezed to excise its contents. Sham animals underwent the same procedure with no ligation or puncture. The abdominal incision was then closed in layers with Ethilon 6.0 suture. Mice were resuscitated with 1.0 ml of Ringer's solution via subcutaneous injection. Animals recovered under a heat lamp for approximately 30 minutes and were allowed food and water ad lib.

Results

After transendothelial migration, neutrophils cross the basal lamina and migrate through the extracellular matrix and into tissue or sites of inflammation. To investigate the effects of rhAPC on neutrophil adhesion to the matrix proteins, a cell adhesion assay was performed on fibronectin (FN)-coated cover glass. Human neutrophils were allowed to adhere to immobilized FN in the presence of the chemoattractant, N-formyl-Met-Leu-Phe (fMLP). The addition of rhAPC significantly reduced fMLP-induced adhesion. To investigate the effects of rhAPC on the migration of neutrophils on matrix proteins, live-cell imaging of neutrophils migrating on fibronectin (FN)-coated cover glass was performed in the presence of fMLP. Cell tracking analysis revealed that fMLP significantly increased the random migration of neutrophils on FN, and the presence of rhAPC dramatically reduced this effect (FIG. 1A).

Figure 1B:
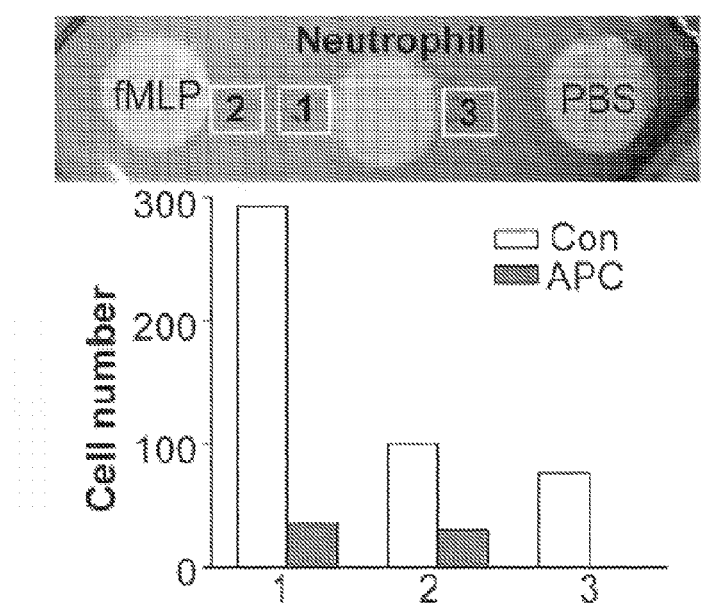
Figure 1C:
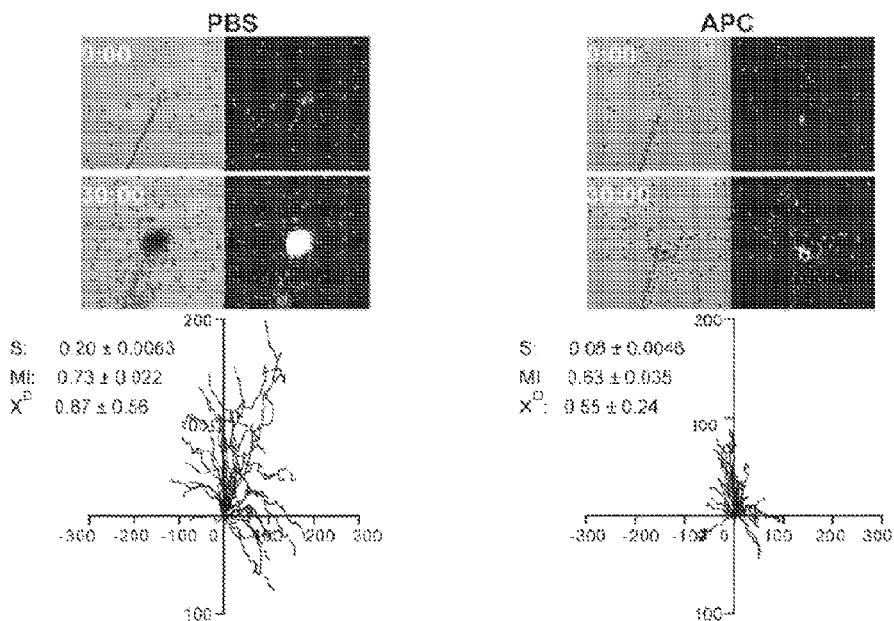

During an infection, chemoattractants are released from various sources including the vascular endothelium, interstitial cells (macrophages and mast cells), and the infectious agent itself. Directional migration of neutrophils toward the chemokine gradients is critical to reach the site of infection. Therefore, the effect of rhAPC on neutrophil directional migration was tested using the under-agarose assay. Neutrophils were seeded in a well flanked by two wells containing either fMLP or PBS (FIG. 1B, upper panel). The majority of neutrophils migrated toward the fMLP-containing well, suggesting that the chemoattractant diffused toward the middle well. As with random migration, rhAPC decreased directional migration of neutrophils on FN towards fMLP (FIG. 1B). The effect of rhAPC on the dynamics of directional neutrophil migration was further investigated using the micropipette assay. In this assay, a micropipette tip containing fMLP was placed in a field of cells to establish a chemokine gradient. Consistent with results obtained using the under-agarose assay, neutrophil migration on FN toward the tip was dramatically decreased by rhAPC pre-treatment (FIG. 1C). Quantitative analysis of over 30 neutrophils in each group revealed that rhAPC decreased the average lateral migration speed (S) more than 2.5 fold, without significantly altering the migratory index (distance from origin/total distance traveled; MI) or the direction of movement (KD) (FIG. 1C). These results indicate that, although neutrophils can sense chemoattractants and become polarized toward chemoattractant gradients in the presence of rhAPC, they cannot move toward the gradient. This was further supported by measurement of intracellular calcium mobilization by fMLP in the presence/absence of rhAPC. Dynamic measurement of intracellular $Ca^{2+}$ showed that rhAPC had no effect on the increase in $Ca^{2+}$ concentration by fMLP treatment (FIG. 1E), suggesting that rhAPC did not functionally alter the signaling pathway associated with chemotaxis receptors on neutrophil.

Figure 1D:
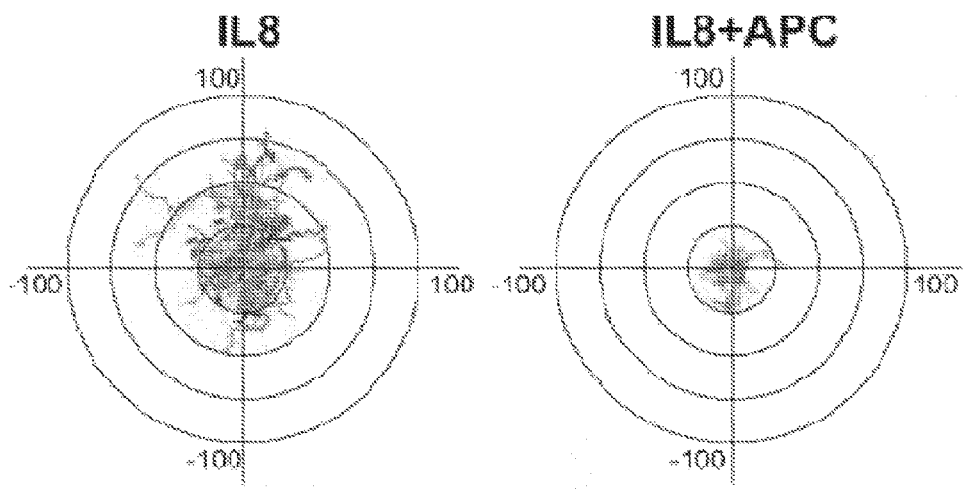
Figure 1E:
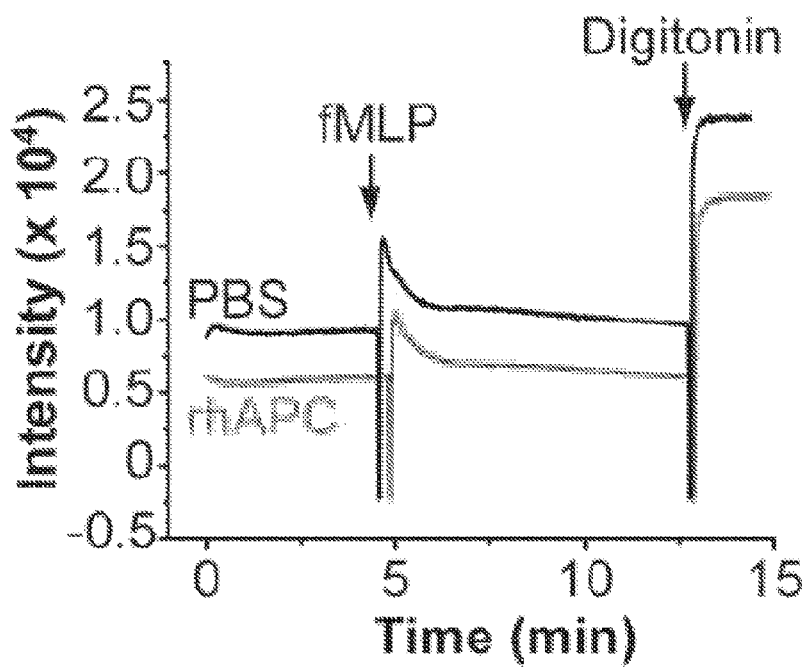
Figure 2A:
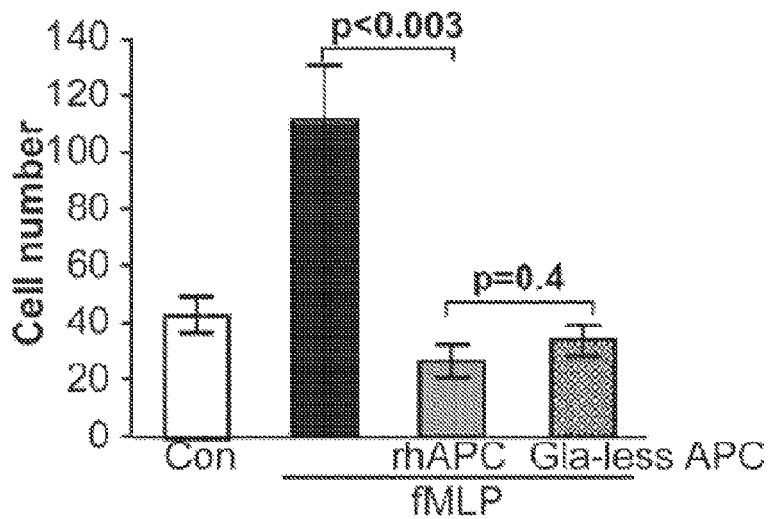
FIGS. 2A-2G show direct binding of rhAPC to neutrophil integrins.

Neutrophils must follow both endogenous and bacterial chemoattractant signals out of the vasculature and through the interstitium to arrive at a site of infection. To investigate whether rhAPC inhibited neutrophil migration induced by host-derived chemoattractants, IL-8 was used in the migration assay. Consistent with results obtained using fMLP, neutrophil migration on FN by IL-8 was dramatically decreased by rhAPC pre-treatment (FIG. 1D). In accord with its ability to block neutrophil migration, rhAPC also abolished the adhesion of human neutrophils to immobilized FN induced by fMLP (FIG. 2A).

Figures 2B, 2C:
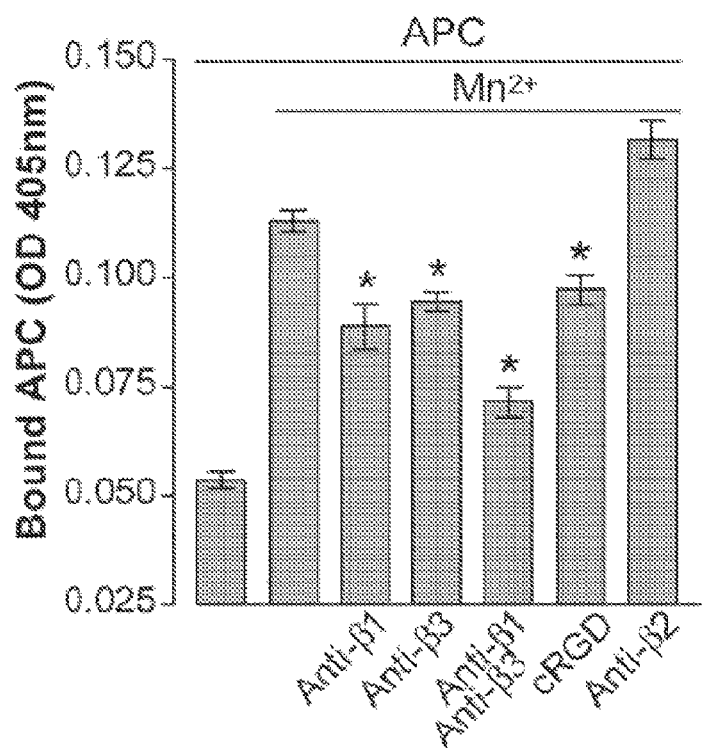

The best characterized integrin binding motif is the RGD sequence, which is present in FN, fibrinogen, von Willebrand factor, vitronectin, and a variety of other adhesion proteins. Many integrins that bind to extracellular protein ligands including α3β1, α5β1, αIIbβ3, and αVβ3, specifically interact with the RGD sequence of their target proteins. As shown in FIG. 2B, amino acid sequence analysis revealed that the catalytic domain of human protein C and APC also contains the RGD sequence. Therefore, it was hypothesized that rhAPC directly interacts with neutrophil integrins to regulate cell migration. To test this hypothesis, rhAPC-binding assays were performed with neutrophils in suspension. The assay buffer containing 1 mM $Ca^{2+}$ and 1 mM $Mg^{2+}$ was supplemented with 1 mM $Mn^{2+}$ to activate cell surface integrins. This significantly increased rhAPC binding to the neutrophil surface (FIG. 2C). The addition of blocking mAbs against β1 or β3 integrins partially displaced rhAPC from the cell surface (FIG. 2C). The presence of both β1 and β3 integrin blocking mAbs further reduced rhAPC binding on neutrophil surface (FIG. 2C). Cyclic RGD peptide also significantly inhibited rhAPC binding, while blocking anti-β2 integrin (non-RGD binding integrin) mAb had no effect (FIG. 2C). Collectively, these results showed that the major mechanism that controls rhAPC binding to the neutrophil surface was through direct interaction with the integrins.

Figure 2D:
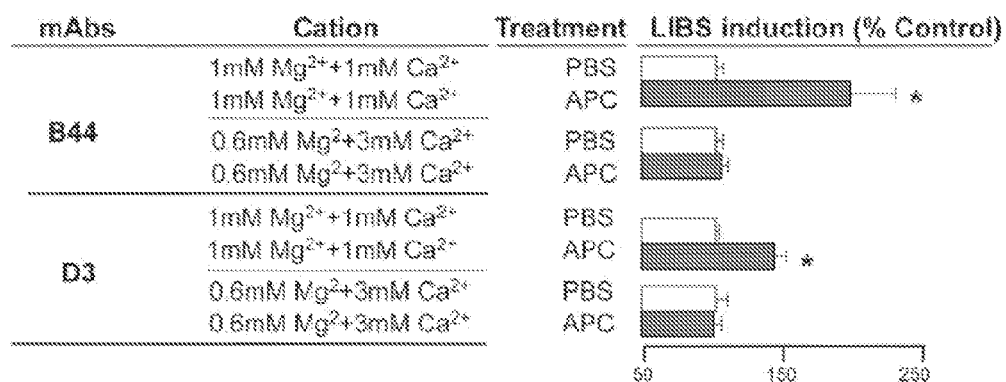

Upon ligand binding, integrins undergo pronounced conformational changes that result in the appearance of ligand-induced binding sites (LIBS), which can be detected by specific monoclonal antibodies. The direct binding of rhAPC to β1 and β3 integrins on intact neutrophils was tested by measuring the appearance of LIBS using B44 mAb (β1 integrin LIBS Ab) and D3 mAb (β3 integrin LIBS Ab). In the presence of 1 mM $Ca^{2+}$ and $Mg^{2+}$, rhAPC strongly induced B44 and D3 binding (FIG. 2D). The binding of APC to EPCR is $Ca^{2+}$-dependent, with ion concentrations of 3 mM $CaCl_2$ and 0.6 mM $MgCl_2$ being optimal for binding (Liaw et al., J. Biol. Chem. 276:8364 (2001)). However, $Ca^{2+}$ has been shown to exert a negative regulatory effect on integrin-ligand binding (Ruoslahti, Annu. Rev. Biochem. 57:375 (1988)). Consistent with this finding, APC did not induce the LIBS Abs binding in the presence of 3 mM $CaCl_2$ and 0.6 mM $MgCl_2$ (FIG. 2D). These data suggested that APC induced conformational changes in neutrophil integrins through direct interaction with the integrins and not through signals resulting from its interaction with EPCR on the neutrophil surface.

Figure 2E:
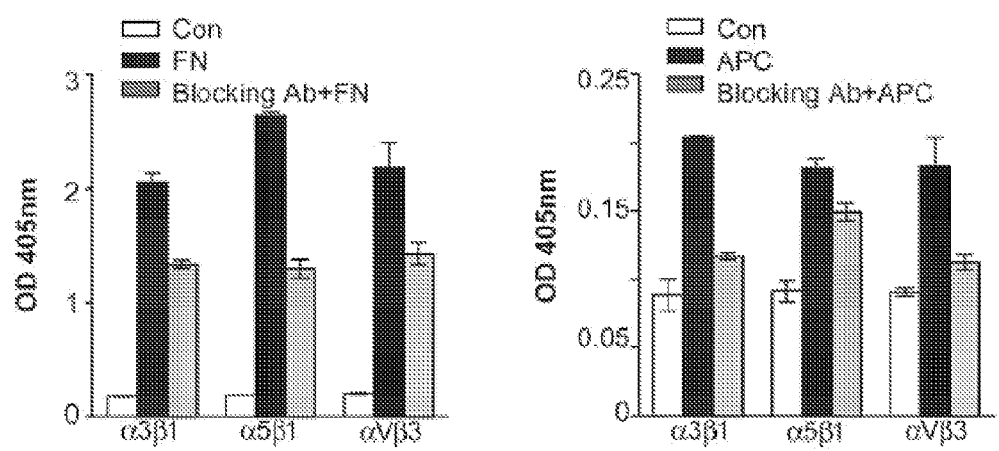

Among the neutrophil integrins that recognize the RGD motif, α3β1, α5β1, and αVβ3 are key in regulating neutrophil chemotaxis (Yauch et al., Mol. Biol. Cell 9:2751 (1998); Burns et al., J. Immunol. 166:4644 (2001); Sixt et al., J. Biol. Chem. 276:18878 (2001)). To test whether APC can bind directly to the integrins, an ELISA-like solid phase receptor-binding assay was performed (FIG. 2E). Soluble α3β1, α5β1, and αVβ3 were captured onto microtiter wells using mAbs specific for β1 or β3. Binding to FN or rhAPC was then measured in buffer containing 1 mM $Mn^{2+}$, 1 mM $Ca^{2+}$, and 1 mM $Mg^{2+}$. As shown in FIG. 2E, FN and rhAPC bound to all three integrins, and this binding was specific, as shown by its reversibility in the presence of integrin-blocking mAbs.

To determine whether rhAPC binds to β1 and β3 integrins through its RGD sequence, the RGD sequence was mutated to RGE (RGE-APC). SDS-PAGE analysis of protein C zymogens prior to and following activation by thrombin indicated that the molecular weight and glycosylation of RGE-APC was similar to that of wild type APC. Enzyme assays using the chromogenic substrate, S-2366, revealed that the Km and kcat of RGE-APC were also comparable to those for wild-type APC (Table 2).

TABLE 2

Enzyme kinetic constants of wild type APC and RGE-APC

|  | rhAPC (WT) | RGE-APC |
|---|---|---|
| $K_m$ | 315 ± 44.43 | 278.20 ± 36.13 |
| $k_{cat}$ | 164.35 ± 13.11 | 146.91 ± 15.37 |
| $k_{cat}/K_m$ | 0.54 ± 0.035 | 0.54 ± 0.024 |

Figure 2F:
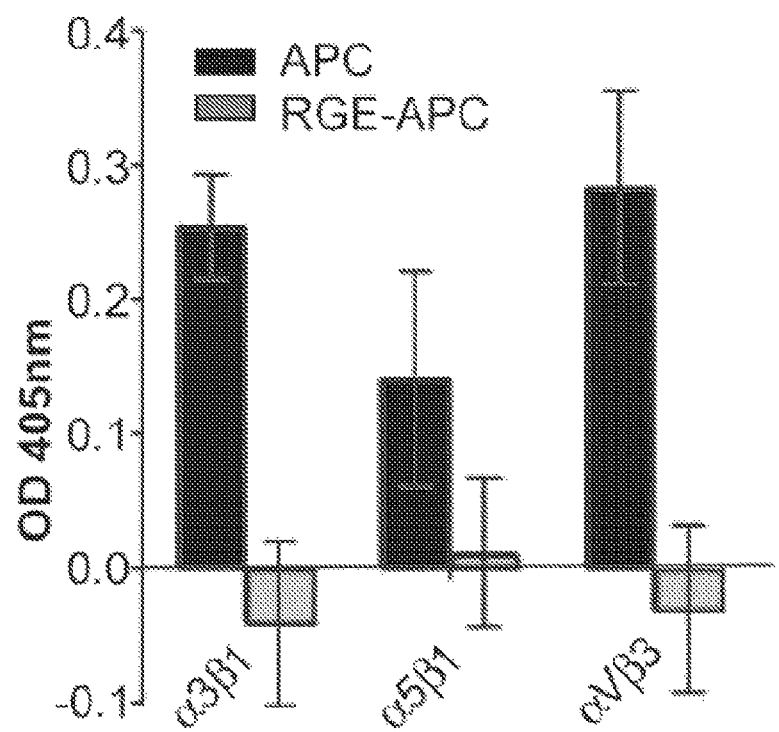
Figure 2G:
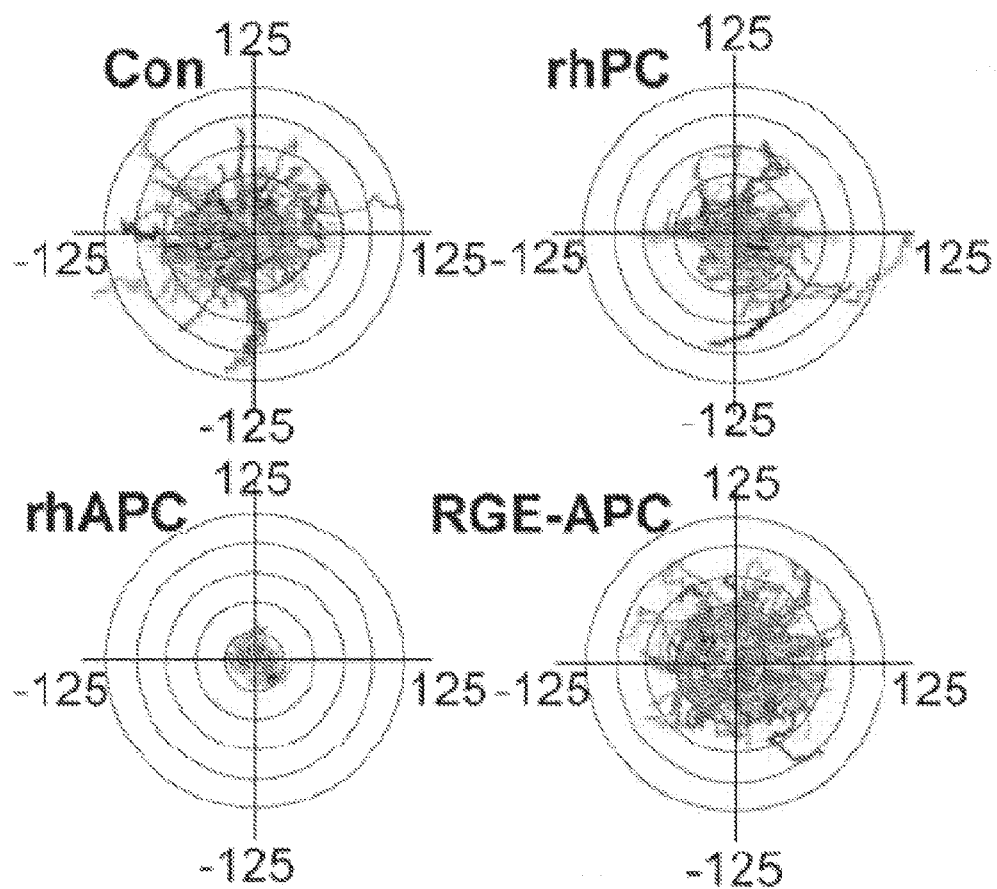

Despite these similarities, the direct binding of RGE-APC to soluble α3β1, α5β1, and αVβ3 integrins was significantly less than that of wild type APC, as measured by the solid phase receptor-binding assays (FIG. 2F). In random migration assay, RGE-APC had no effect on the migration of neutrophils on FN, while the presence of wild type rhAPC dramatically reduced the migration (FIG. 2G). To investigate whether activation of PC is required for the inhibition of neutrophil migration and adhesion, the zymogen PC (rhPC) was tested in migration and adhesion assays. Unlike rhAPC, rhPC failed to block neutrophil migration on FN (FIG. 2G) and also failed to block neutrophil adhesion. The recombinant APC variant S360A-APC, however, which lacks proteolytic activity (Gale et al., Protein Sci. 6:132-140 (1997)) successfully inhibited neutrophil migration. Thus, these data show that the RGD sequence in rhAPC was an essential feature of its direct interaction with the neutrophil integrins and for inhibition of neutrophil migration on matrix proteins. These data also show that APC's enzymatic proteolytic activity is not necessary for the inhibition.

Figure 3A:
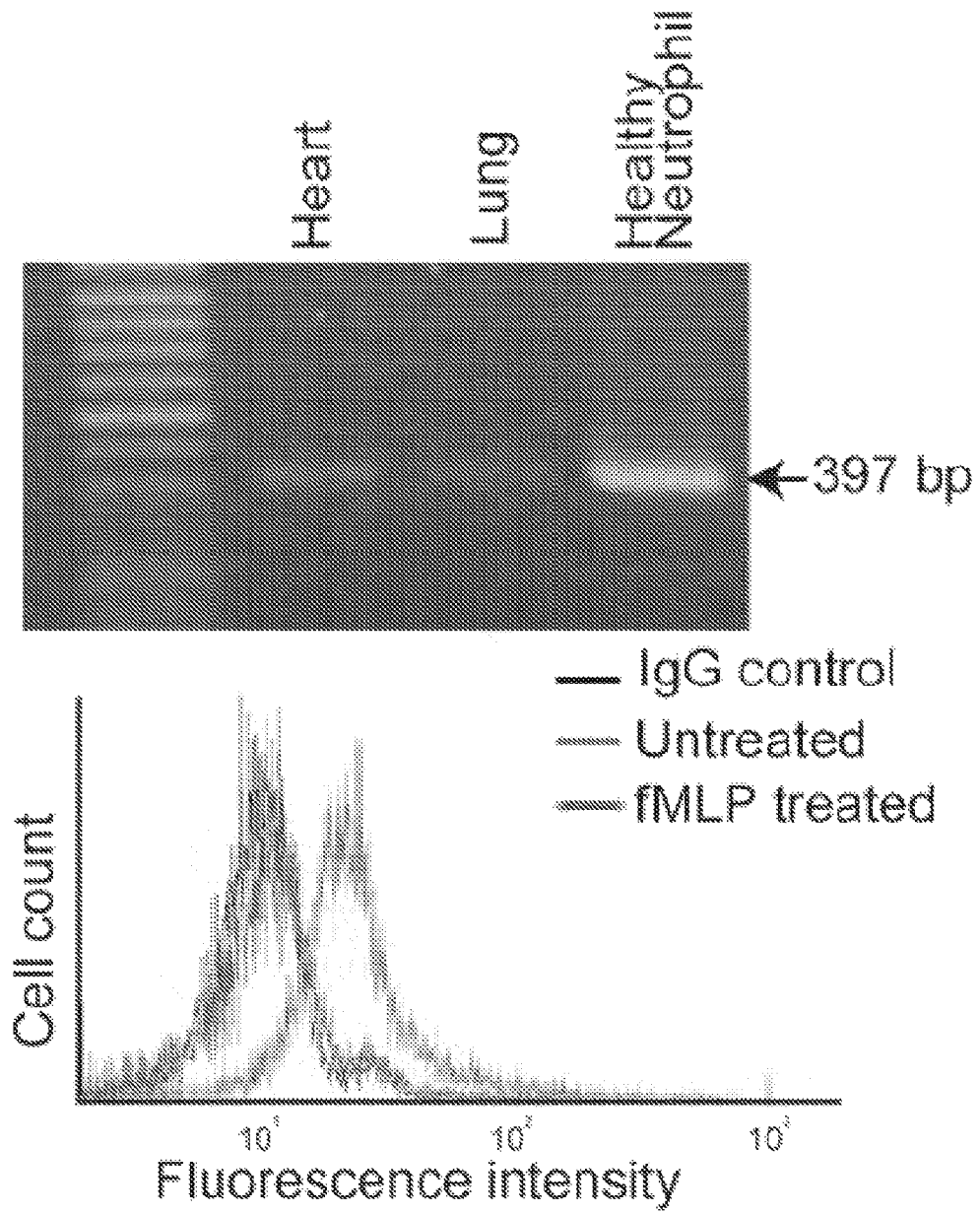
FIGS. 3A-3F show simultaneous binding of rhAPC to neutrophil integrins and EPCR.

EPCR was the first identified cellular APC receptor and is expressed in healthy human neutrophils and monocytes (Sturn et al., Blood 102:1499 (2003)). Because activated neutrophils contribute to organ system dysfunction and mortality in sepsis, we first compared EPCR expression between unstimulated and fMLP-stimulated neutrophils. Reverse-transcription PCR revealed that healthy neutrophils expressed EPCR mRNA (FIG. 3A). Cell surface expression of EPCR could also be detected in these cells, although the overall levels of the receptor were very low (FIG. 3A). Stimulation with fMLP dramatically enhanced cell surface expression of EPCR (FIG. 3A).

Figure 3B:
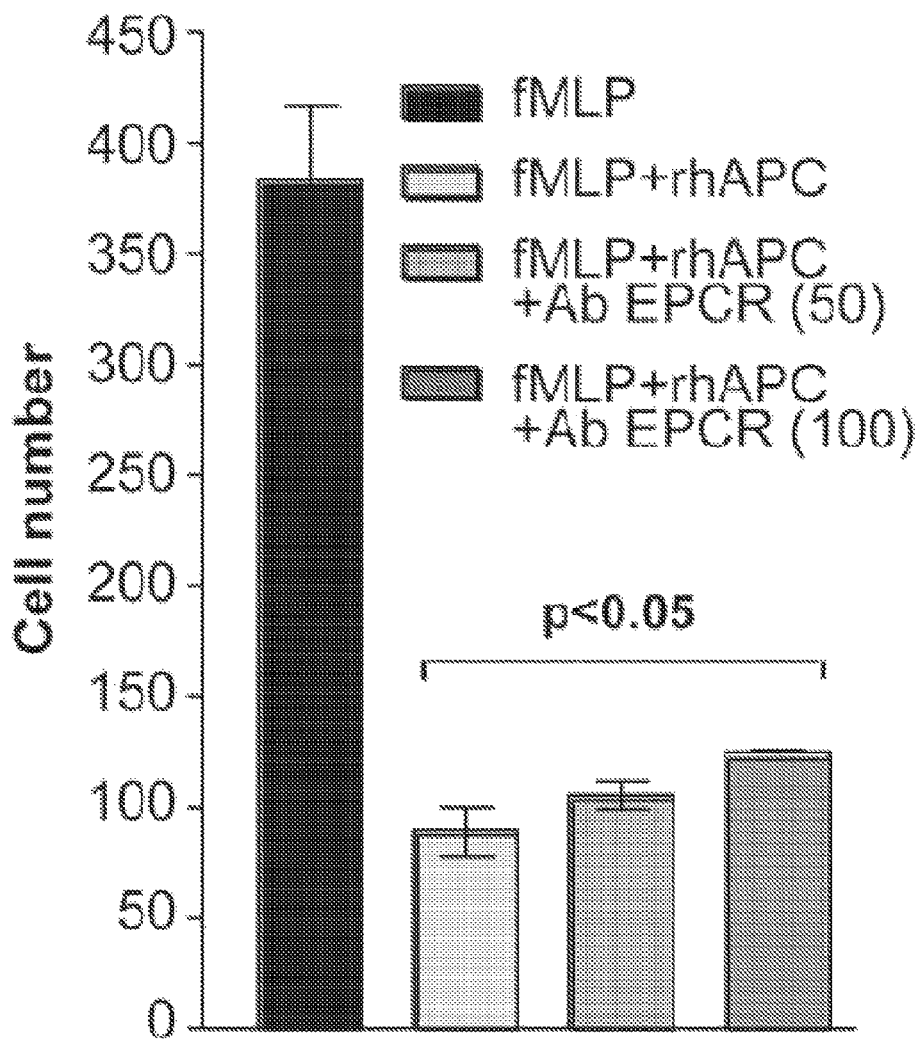
Figure 3C:
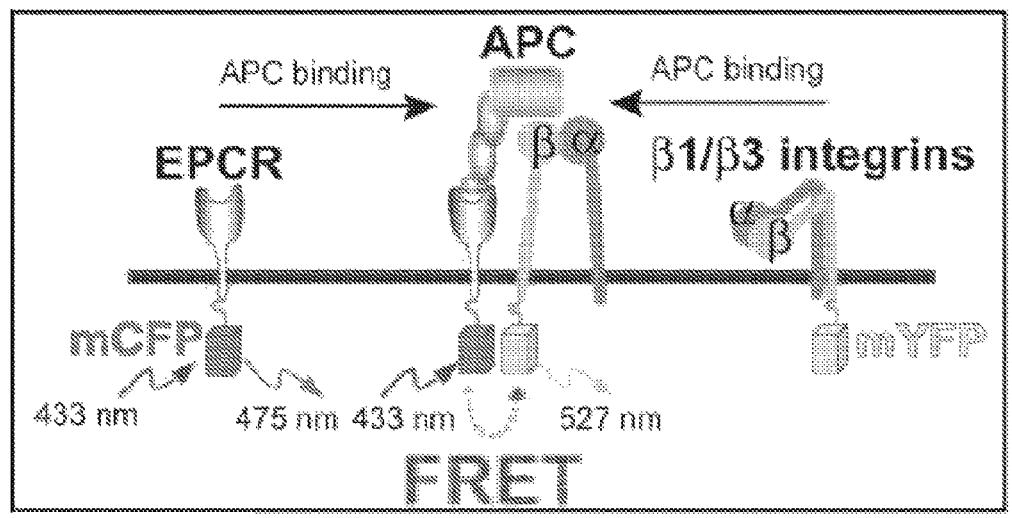
Figure 3D:
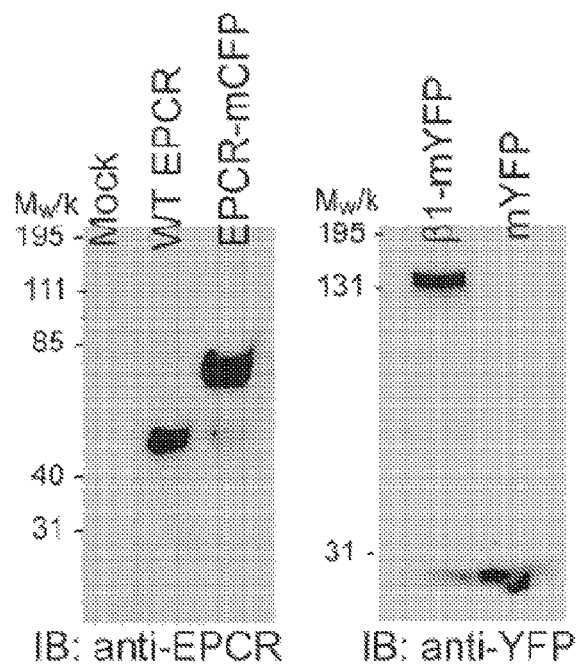
Figure 3E:
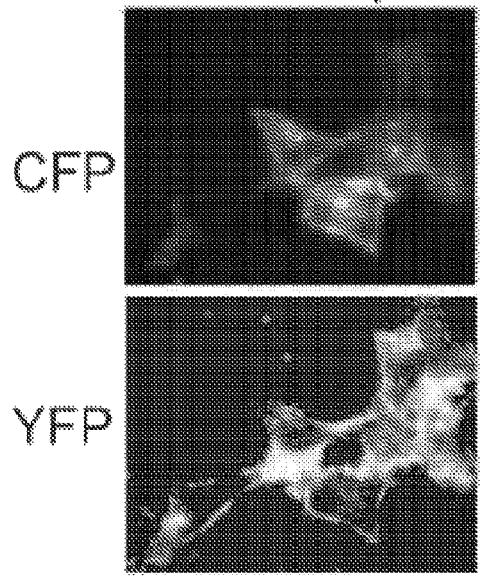
Figure 3F:
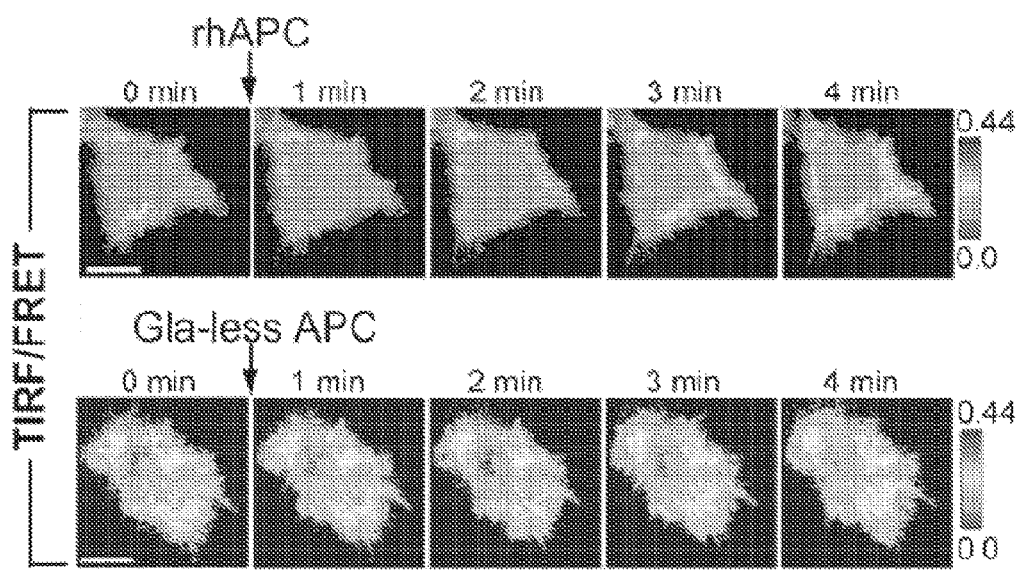

Previously, it was shown that neutrophil migration through nitrocellulose micropore filter (without any protein coatings) was inhibited by rhAPC and the inhibition was reversed by an EPCR blocking Ab (Sturn et al., Blood 102:1499 (2003)). However, in our neutrophil adhesion assay to immobilized FN, Gla-less APC, a mutant form of APC that lacks the EPCR binding motif (Regan et al., J. Biol. Chem. 272:26279 (1997)), inhibited adhesion to a slightly less, but similar, degree as the wild type protein (FIG. 2A). Therefore, it was tested whether the anti-EPCR antibody relieved the rhAPC-induced inhibition of neutrophil adhesion on FN. Blocking of neutrophil EPCR with high concentration of antibody only partially, but significantly, reversed the inhibitory effect of rhAPC on neutrophil binding to FN (FIG. 3B). In endothelial cells, EPCR-bound APC can mediate signals through PAR-1 (Riewald et al., Science 296:1880 (2002)) and S1P1 receptors (Feistritzer and Riewald, Blood 105:3178 (2005); Finigan et al., J. Biol. Chem. 280:17286 (2005)). However, agonists of PAR-1 (SFLLRNPNDKYEPF (SEQ ID NO:39)) and S1P1 (SEW2871) did not reverse the inhibitory effect of rhAPC on neutrophil migration. Thus these results show that rhAPC can bind to EPCR and β1/β3 integrins simultaneously on the neutrophil surface (FIG. 3C), where EPCR provides a supportive role for the integrin binding. To investigate the double occupation of rhAPC on living cell surface, fluorescence resonance energy transfer (FRET) analysis was employed to measure the energy transfer between monomeric yellow fluorescent protein (mYFP) and monomeric cyan fluorescent protein (mCFP) as a function of distance (FIG. 3C). A C-terminal CFP-tagged EPCR (EPCR-mCFP) and YFP-tagged β1 integrin (β1-mYFP) were constructed (FIGS. 3C and 3D). EPCR-mCFP and β1-mYFP were transiently co-transfected into the EPCR deficient HEK293, where they localized predominantly to the plasma membrane (FIG. 3E). To test if there was a decrease in the distance between EPCR and β1 integrins by rhAPC ligation, dynamic FRET was used to measure changes in the relative proximity of these cell surface proteins in the presence of rhAPC or GLA-less APC. Since the ligand will only bind to cell surface receptors, optical measurements were confined to the plasma membrane using through the objective total internal reflection fluorescence (TIRF). Dynamic FRET measurements on TIRF microscopy showed a significant increase in FRET efficiency after rhAPC treatment (FIG. 3F). No obvious FRET change was observed with Gla-less APC (FIG. 3F). Therefore these data support the hypothesis that rhAPC recruits EPCR and β1 integrins in close proximity, within 100 Å, on cell membrane through simultaneous binding to EPCR and the integrins.

Figure 4A:
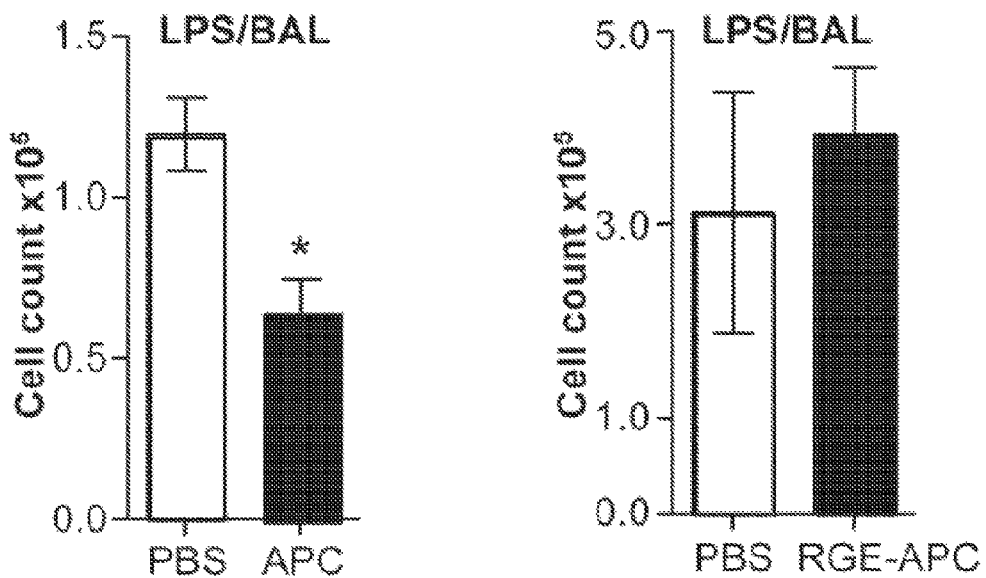
FIGS. 4A-4C show the RGD sequence of rhAPC is critical for inhibition of neutrophil migration in vivo.
Figure 4B:
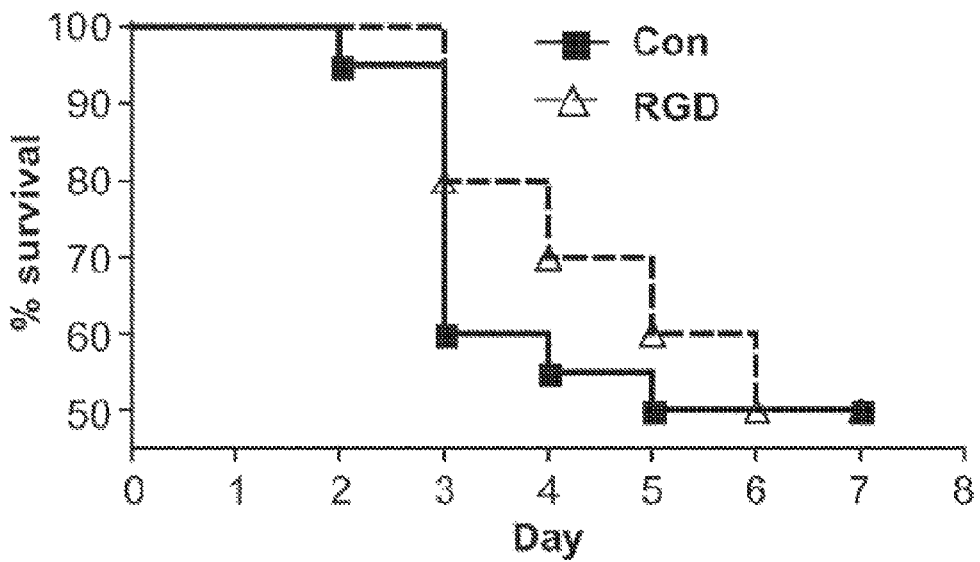
Figure 4C:
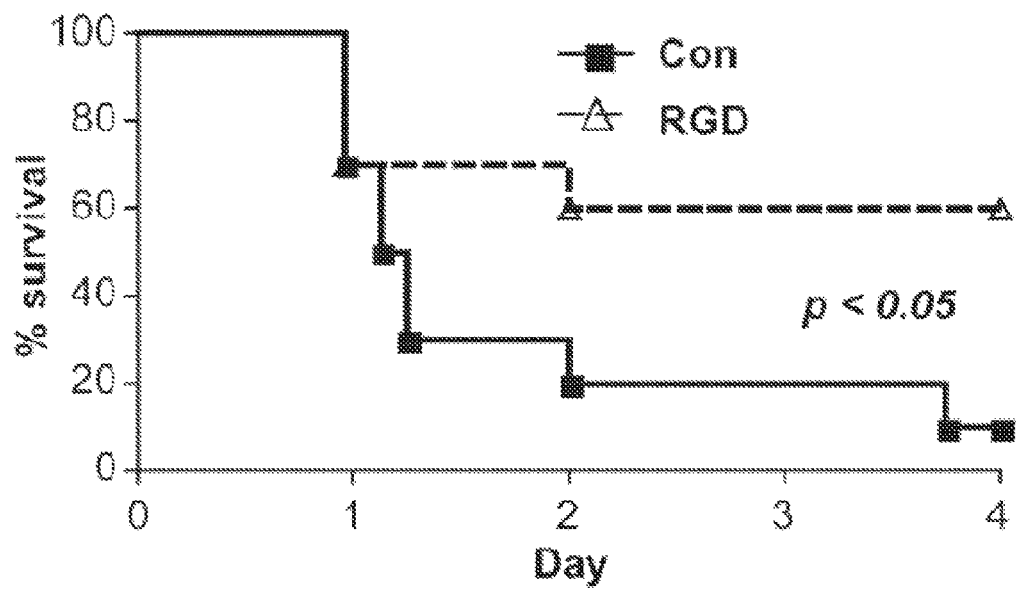

Intravenous administration of rhAPC is known to reduce lipopolysaccharide (LPS)-induced pulmonary inflammation by attenuating neutrophil chemotaxis towards the alveolar compartment. To show that the protective effect of rhAPC in vivo is associated with its interaction with neutrophil integrins and its suppression of neutrophil migration, LPS instillation induced neutrophil recruitment into bronchioalveolar lavage fluid (BALF) was determined by flow cytometry. Neutrophil recruitment in the BALF was significantly reduced by rhAPC, but not by RGE-APC, injection (FIG. 4A). To further prove that the RGD sequence in rhAPC is important for its beneficial effects in sepsis, cecal ligation and puncture (CLP) was induced and the survivals of septic mice were measured in the absence or presence of a RGD peptide that has high affinity to both β1 and β3 integrins (acetyl-c[(penicillamine)-O-methyltyrosine-ARGDN(tetrahydroisoquinoline-3-carboxylic acid)C]—NH$_2$; Mattern et al., Cancer Ther. 3A:325 (2005)). In 'mid-grade' sepsis (50% survival) (Rittirsch et al., Nat. Med. 14:551 (2008)), treatment of mice with the RGD peptide reproducibly prolonged the time of survival, but there was no significant change in the 7-day mortality (FIG. 4B). Administration of rhAPC significantly reduced mortality in a subset of patients with severe sepsis (Bernard et al., N. Engl. J. Med. 344:699 (2001)), and currently it is indicated for use in patients with sepsis involving acute organ dysfunction and a high risk of death. In order to examine whether the RGD peptide alters mortality in 'high-grade' sepsis, 90% mortality was induced by endotoxemia. When LPS was given at $LD_{90}$, a single dose of the RGD peptide reduced mortality from 90 to 60% (FIG. 4C). These findings demonstrated that the blocking of integrins by rhAPC was critical for the inhibition of neutrophil recruitment and for the protection in sepsis.

Given the complexity of the systemic inflammatory response to infection, it is not surprising that many targeted therapies in sepsis have not been able to improve survival. rhAPC was the first drug approved by the FDA for this indication but its broad application has been questioned. Nonetheless, improvements in current APC therapy and development of better targeted, more efficient anti-sepsis therapies have been hampered by a lack of understanding of the exact mechanisms underlying the beneficial effects of rhAPC on organ function and survival rate in sepsis. The results presented here demonstrate that rhAPC inhibits neutrophil adhesion and migration on extracellular matrix proteins by directly binding to integrins (β1 and β3 integrins) at the neutrophil surface. Therefore, leukocyte integrins are cellular receptors for rhAPC and specific APC-integrin interactions inhibit neutrophil migration. If the beneficial effects of rhAPC on sepsis are mediated, in part, by diminishing integrin-mediated neutrophil infiltration into the inflamed tissue, then anti-integrin reagents may be used as therapies for severe sepsis or as a combination therapy with rhAPC to improve the clinical outcomes of rhAPC treatment.

Example 2 rhAPC Mutants with High Affinity for Integrins

If the primary effects of rhAPC on sepsis are attributable both to protection of endothelium and to changes in integrin-mediated neutrophil migration, then modifications of rhAPC that have higher affinity to the neutrophil integrins, and still affect endothelial function through the EPCR, may result in a more potent and better-targeted anti-sepsis therapy.

Figure 5:
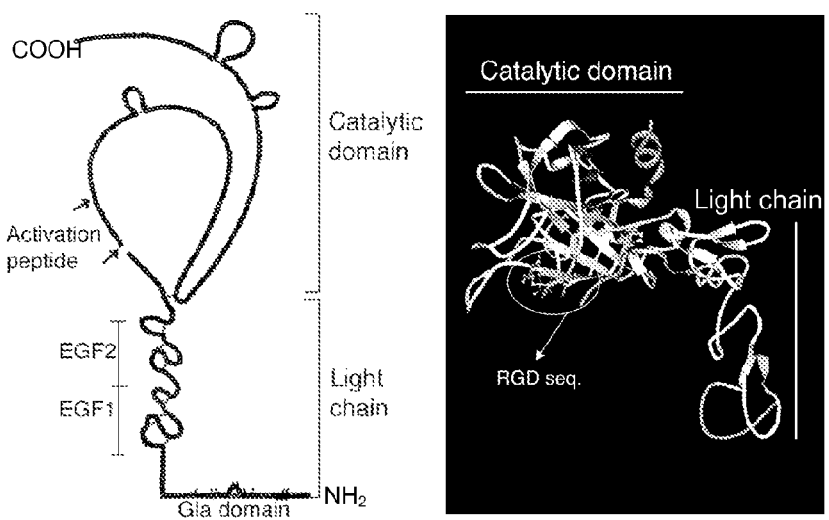
FIG. 5 shows two-dimensional (2D) and three-dimensional (3D) structures of APC.

The crystal structures of the complex of RGD peptide and integrin αVβ3 have been solved. The peptide binds with its Arg contacting the α subunit/β propeller domain and its Asp ligated to a $Mn^{2+}$ held in the metal ion-dependent adhesion site (MIDAS) of the β subunit I-like domain. The calculated buried area of the RGD motif in the αVβ3 crystal is 373 Å, which is close to the reported value, 355 Å. The solvent accessible surface area of rhAPC RGD motif was calculated, which is comparable to the buried area of the complex. The solvent accessible surface area of rhAPC RGD motif was 140 Å. A main reason for the small buried area was that the light chain covers a part of the RGD motif in the catalytic domain (FIG. 5).

Specifically, the C-terminal of the light chain covered the RGD motif of the catalytic domain. The light chain was removed and the buried area of the rhAPC RGD motif was recalculated. The buried area of the RGD motif was 208 Å. However, the area of the RGD motif was still smaller than that of αVβ3 (Table 3).

TABLE 3

RGD Motif Surface Accessible Areas.

| | Buried Area | | | |
|---|---|---|---|---|
| | R | G | D | Sum |
| αVβ3 + RGD (1L5G.pdb) | 163.07 | 66.2 | 144.41 | 373.68 |
| APC (1AUT.pdb): with light chain | 88.92 | 13/19 | 38.34 | 140.45 |
| APC (1AUT.pdb): without light chain | 91.42 | 39.03 | 78.28 | 208.73 |

These data show that accessibility of the RGD motif in wild type rhAPC was not optimal for integrin binding.

The structures of rhAPC RGD motif and RGD peptide in complex were compared with αVβ3. The coordinates were superimposed and it was found that the two structures are different. The rhAPC RGD motif had a different side-chain orientation compared to the αVβ3 RGD motif, which suggested the presence of potential steric clash when the wild type rhAPC RGD motif binds to the integrins.

To increase the affinity of APC for integrins, the accessibility and structure of the RGD motif was altered. As mentioned above, the conformation of the RGD motif was not optimal for integrin binding. Therefore, subtle conformational changes around the area were used to enhance the affinity of APC to the integrins.

Figure 6:
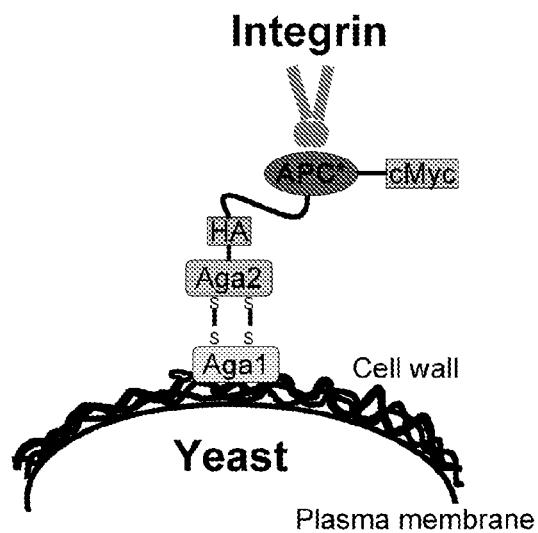
FIG. 6 is a schematic drawing of the expression of the protein of interest as a fusion to agglutinin in a yeast display system.

A broad-range of hosts and scaffolds based on ribosome display, phage display, and cell-surface display are used widely as systems to implement directed evolution (Hoogenboom, Nat. Biotechnol. 23:1105 (2005)). Among the cell surface display systems based on microbial and eukaryotic hosts, the yeast system offers the unique advantage of eukaryotic machinery that enables post-translational modification, glycosylation, and disulfide isomerization (Wittrup, Curr. Opin. Biotechnol. 12:392 (2001)). The yeast surface display was used to screen variants of high affinity rhAPC. The yeast display system that was used employs the α-agglutinin yeast adhesion receptor to display recombinant proteins on cell surface of S. cerevisiae. The receptor consists of two proteins, Aga1 and Aga2 (FIG. 6). Aga1 is secreted and becomes covalently attached to β-glucan in the extracellular matrix of the yeast cell wall. Aga2 binds to Aga1 through two disulfide bonds, making it possible to express a protein of interest fused to Aga2.

A cDNA library was constructed by error-prone PCR using nucleotide analogues and a mutagenesis kit (GeneMorph® II Random Mutagenesis Kit, Stratagene, La Jolla, Calif.) to introduce a comparable ratio of transition (purine to purine or pyrimidine to pyrimidine) to transversion (purine to pyrimidine or pyrimidine to purine) mutations. Mixtures of 1 μg cDNA library and 0.5 μg of the Nhe1/BamH1 linearized pCTCON vector in 5 μl were transformed into $10^8$ yeast cells by electroporation, which lead to ~$10^6$ diversity in the library. Inside the cells, the cDNA library was recombined into the vector by the endogenous Gap repair protein. The yeast library of the human protein C was activated by thrombin. Progressive enrichment of cells encoding high affinity APC was done by panning Yeast cells that display APC variants were allowed to bind to β1 and β3 integrin expressing HEK293T cells. Yeast cells with high affinity APC remained bound, while others were removed by washing. Those that remained were eluted for further analysis.

Figure 7A:
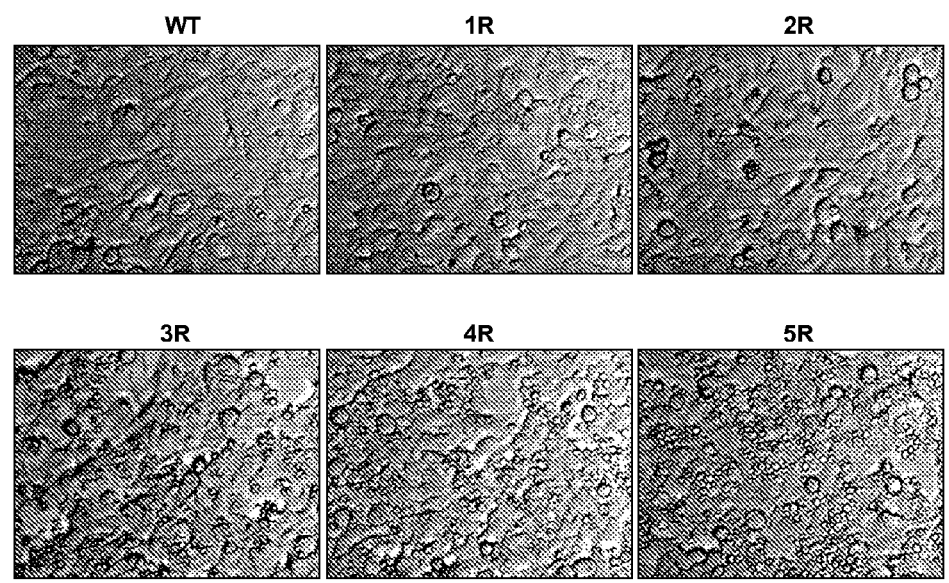
FIGS. 7A and 7B show cycles of panning of a yeast library on HEK293 cells.
Figure 7B:
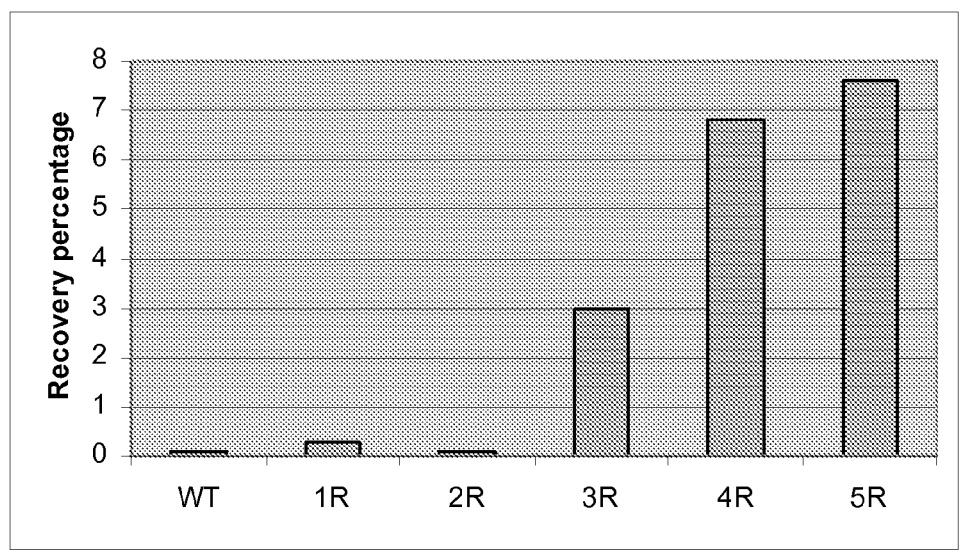
Figure 8:
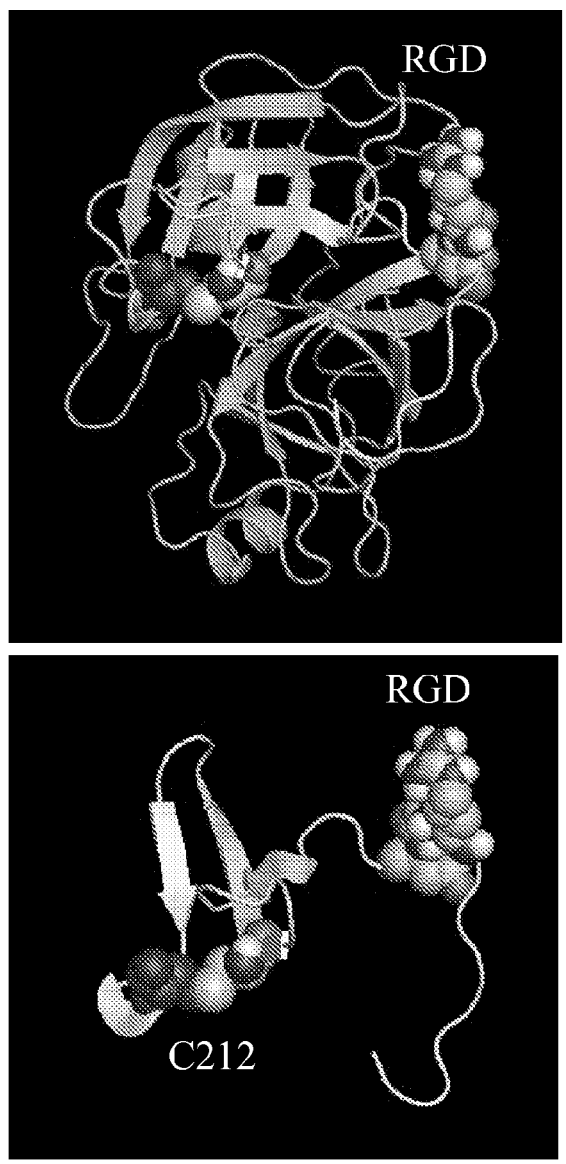
FIG. 8 shows the location of the C212R mutation.

The mutant APC yeast library was selected by panning on HEK293T cells. After five cycles of panning (FIGS. 7A and 7B), the percentage of cells that bound to HEK293T cells was dramatically increased. A total of 20 yeast colonies selected with panning were sequenced. Of these, 12 had unique sequences and were designated as C212R (the amino acid sequence was numbered as described (Mather et al., EMBO J. 15:6822 (1996))) (FIG. 8). This mutation is distantly located from the RGD motif. However, the disulfide bond formed by C212 connects anti-parallel beta-sheets, which are directly connected to the loops including RGD motif. Therefore, the mutation could destabilize the structure and expose the RGD motif for more favorable integrin binding.

A second panning of the mutant APC yeast library on HEK293T cells was performed. After five cycles of panning, the percentage of cells bound to HEK293T cells was dramatically increased. More than 50 yeast colonies selected with the second round of panning were sequenced. Of these, 12 had the unique sequence designated as D172N (SEQ ID NO:43). This mutation is distantly located from the RGD motif.

Figure 9A:
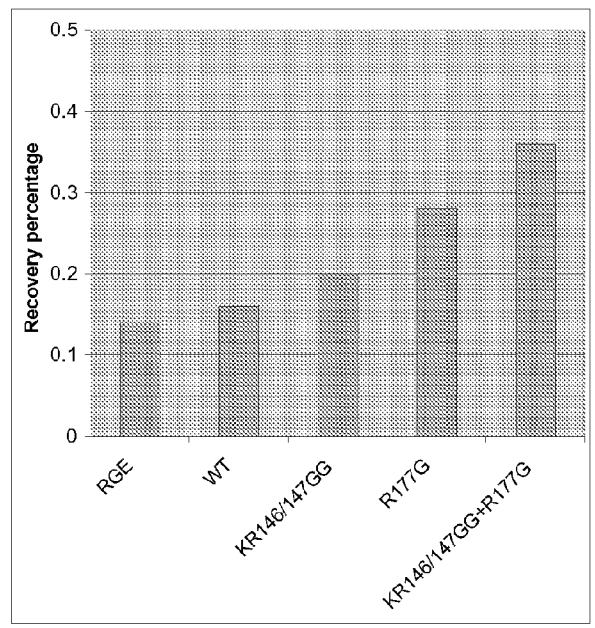
FIG. 9A shows the locations of KR146/147GG and R177G.
Figure 9B:
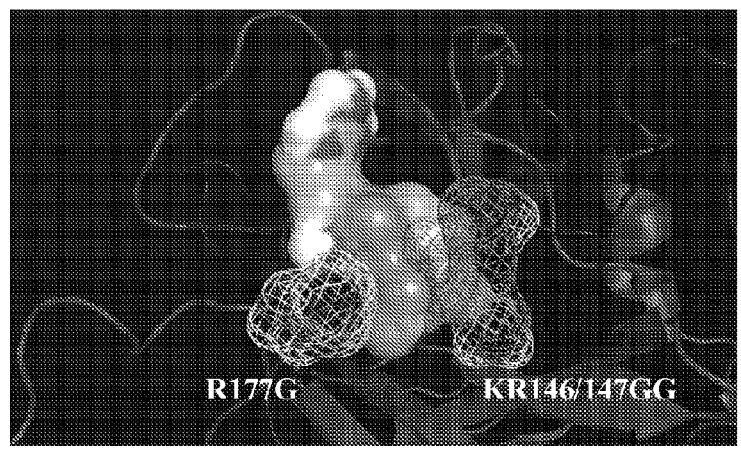
FIG. 9B shows a histogram of binding of yeast that express mutant APCs on HEK293 cells.

A rational design approach to generate high affinity mutant APC was also employed. According to the crystal structure of human APC, several neighboring positive charged amino acids form hydrogen bonds with the RGD sequence. Mutations to remove the hydrogen bonds were constructed and displayed on the yeast surface. Mutant APCs, KR146/147GG-APC and R177G-APC, showed enhanced binding compared to WT APC (FIG. 9A). When these mutations were combined (KR146/147GG+R177G), the adhesion was further enhanced (FIGS. 9A and 9B). An additional mutation, K146R, was also identified. The data suggest that these point mutations increased the affinity of APC to integrins.

What is claimed is:

1. An isolated polypeptide comprising an amino acid sequence that is at least 95% identical to the amino acid sequence set forth in SEQ ID NO: 1 and one or more amino acid substitutions selected from the group consisting of K146R, C212R, K146G, R147G, and R177G; wherein said isolated polypeptide is an activated protein C with serine protease activity.

2. The isolated polypeptide of claim 1, wherein said isolated polypeptide comprises the amino acid substitution(s) selected from the group consisting of K146G and R147G; R177G, K146G, and R147G; C212R, K146G, and R147G; C212R and R177G; and K146R.

3. The isolated polypeptide of claim 1, wherein said isolated polypeptide further comprises the amino acid substitutions selected from the group consisting of RR229/230AA; KKK191-193AAA; and KKK191-193AAA and RR229/230AA.

4. A composition comprising the isolated polypeptide of claim 1 and a pharmaceutically acceptable excipient.

5. A method of treating sepsis in a subject comprising administering the isolated polypeptide of claim 1 to a subject having sepsis.

* * * * *

SEQUENCE LISTING

```
<160> NUMBER OF SEQ ID NOS: 43

<210> SEQ ID NO 1
<211> LENGTH: 419
<212> TYPE: PRT
<213> ORGANISM: Homo sapiens

<400> SEQUENCE: 1

Ala Asn Ser Phe Leu Glu Glu Leu Arg His Ser Ser Leu Glu Arg Glu
  1               5                  10                  15

Cys Ile Glu Glu Ile Cys Asp Phe Glu Glu Ala Lys Glu Ile Phe Gln
                 20                  25                  30

Asn Val Asp Asp Thr Leu Ala Phe Trp Ser Lys His Val Asp Gly Asp
             35                  40                  45

Gln Cys Leu Val Leu Pro Leu Glu His Pro Cys Ala Ser Leu Cys Cys
         50                  55                  60

Gly His Gly Thr Cys Ile Asp Gly Ile Gly Ser Phe Ser Cys Asp Cys
 65                  70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
```

```
            225                 230                 235                 240
Lys Glu Val Phe Val His Pro Asn Tyr Ser Lys Ser Thr Thr Asp Asn
                    245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
            275                 280                 285

Asn Gln Ala Gly Gln Glu Thr Leu Val Thr Gly Trp Gly Tyr His Ser
            290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                    325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
            370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                    405                 410                 415

Trp Ala Pro

<210> SEQ ID NO 2
<211> LENGTH: 461
<212> TYPE: PRT
<213> ORGANISM: Homo sapiens

<400> SEQUENCE: 2

Met Trp Gln Leu Thr Ser Leu Leu Leu Phe Val Ala Thr Trp Gly Ile
 1               5                  10                  15

Ser Gly Thr Pro Ala Pro Leu Asp Ser Val Phe Ser Ser Ser Glu Arg
                20                  25                  30

Ala His Gln Val Leu Arg Ile Arg Lys Arg Ala Asn Ser Phe Leu Glu
            35                  40                  45

Glu Leu Arg His Ser Ser Leu Glu Arg Glu Cys Ile Glu Glu Ile Cys
        50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
            100                 105                 110

Asp Gly Ile Gly Ser Phe Ser Cys Asp Cys Arg Ser Gly Trp Glu Gly
            115                 120                 125

Arg Phe Cys Gln Arg Glu Val Ser Phe Leu Asn Cys Ser Leu Asp Asn
            130                 135                 140

Gly Gly Cys Thr His Tyr Cys Leu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
```

```
            180                 185                 190
Lys Arg Ser His Leu Lys Arg Asp Thr Glu Asp Gln Glu Asp Gln Val
            195                 200                 205
Asp Pro Arg Leu Ile Asp Gly Lys Met Thr Arg Gly Asp Ser Pro
            210                 215                 220
Trp Gln Val Val Leu Leu Asp Ser Lys Lys Lys Leu Ala Cys Gly Ala
225                 230                 235                 240
Val Leu Ile His Pro Ser Trp Val Leu Thr Ala Ala His Cys Met Asp
            245                 250                 255
Glu Ser Lys Lys Leu Leu Val Arg Leu Gly Glu Tyr Asp Leu Arg Arg
            260                 265                 270
Trp Glu Lys Trp Glu Leu Asp Leu Asp Ile Lys Glu Val Phe Val His
            275                 280                 285
Pro Asn Tyr Ser Lys Ser Thr Thr Asp Asn Asp Ile Ala Leu Leu His
            290                 295                 300
Leu Ala Gln Pro Ala Thr Leu Ser Gln Thr Ile Val Pro Ile Cys Leu
305                 310                 315                 320
Pro Asp Ser Gly Leu Ala Glu Arg Glu Leu Asn Gln Ala Gly Gln Glu
            325                 330                 335
Thr Leu Val Thr Gly Trp Gly Tyr His Ser Ser Arg Glu Lys Glu Ala
            340                 345                 350
Lys Arg Asn Arg Thr Phe Val Leu Asn Phe Ile Lys Ile Pro Val Val
            355                 360                 365
Pro His Asn Glu Cys Ser Glu Val Met Ser Asn Met Val Ser Glu Asn
            370                 375                 380
Met Leu Cys Ala Gly Ile Leu Gly Asp Arg Gln Asp Ala Cys Glu Gly
385                 390                 395                 400
Asp Ser Gly Gly Pro Met Val Ala Ser Phe His Gly Thr Trp Phe Leu
            405                 410                 415
Val Gly Leu Val Ser Trp Gly Glu Gly Cys Gly Leu Leu His Asn Tyr
            420                 425                 430
Gly Val Tyr Thr Lys Val Ser Arg Tyr Leu Asp Trp Ile His Gly His
            435                 440                 445
Ile Arg Asp Lys Glu Ala Pro Gln Lys Ser Trp Ala Pro
            450                 455                 460

<210> SEQ ID NO 3
<211> LENGTH: 419
<212> TYPE: PRT
<213> ORGANISM: Homo sapiens

<400> SEQUENCE: 3

Ala Asn Ser Phe Leu Glu Glu Leu Arg His Ser Ser Leu Glu Arg Glu
1               5                   10                  15
Cys Ile Glu Glu Ile Cys Asp Phe Glu Glu Ala Lys Glu Ile Phe Gln
            20                  25                  30
Asn Val Asp Asp Thr Leu Ala Phe Trp Ser Lys His Val Asp Gly Asp
            35                  40                  45
Gln Cys Leu Val Leu Pro Leu Glu His Pro Cys Ala Ser Leu Cys Cys
            50                  55                  60
Gly His Gly Thr Cys Ile Asp Gly Ile Gly Ser Phe Ser Cys Asp Cys
65                  70                  75                  80
Arg Ser Gly Trp Glu Gly Arg Phe Cys Gln Arg Glu Val Ser Phe Leu
            85                  90                  95
```

```
Asn Cys Ser Leu Asp Asn Gly Gly Cys Thr His Tyr Cys Leu Glu Glu
             100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Arg Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 4
<211> LENGTH: 419
<212> TYPE: PRT
<213> ORGANISM: Homo sapiens

<400> SEQUENCE: 4

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45
```

```
Gln Cys Leu Val Leu Pro Leu Glu His Pro Cys Ala Ser Leu Cys Cys
 50                  55                  60

Gly His Gly Thr Cys Ile Asp Gly Ile Gly Ser Phe Ser Cys Asp Cys
 65                  70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
                100                 105                 110

Val Gly Trp Arg Arg Cys Ser Cys Ala Pro Gly Tyr Lys Leu Gly Asp
                115                 120                 125

Asp Leu Leu Gln Cys His Pro Ala Val Lys Phe Pro Cys Gly Arg Pro
            130                 135                 140

Trp Gly Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
                180                 185                 190

Lys Leu Ala Cys Gly Ala Val Leu Ile His Pro Ser Trp Val Leu Thr
                195                 200                 205

Ala Ala His Cys Met Asp Glu Ser Lys Lys Leu Leu Val Arg Leu Gly
            210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
                260                 265                 270

Ile Val Pro Ile Cys Leu Pro Asp Ser Gly Leu Ala Glu Arg Glu Leu
                275                 280                 285

Asn Gln Ala Gly Gln Glu Thr Leu Val Thr Gly Trp Gly Tyr His Ser
                290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
                355                 360                 365

His Gly Thr Trp Phe Leu Val Gly Leu Val Ser Trp Gly Glu Gly Cys
                370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 5
<211> LENGTH: 419
<212> TYPE: PRT
<213> ORGANISM: Homo sapiens

<400> SEQUENCE: 5
```

```
Ala Asn Ser Phe Leu Glu Glu Leu Arg His Ser Ser Leu Glu Arg Glu
 1               5                  10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
 50                  55                  60

Gly His Gly Thr Cys Ile Asp Gly Ile Gly Ser Phe Ser Cys Asp Cys
 65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
            130                 135                 140

Trp Lys Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
            165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
            195                 200                 205

Ala Ala His Cys Met Asp Glu Ser Lys Lys Leu Leu Val Arg Leu Gly
            210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
            245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
            275                 280                 285

Asn Gln Ala Gly Gln Glu Thr Leu Val Thr Gly Trp Gly Tyr His Ser
            290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
            325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
            370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
            405                 410                 415

Trp Ala Pro
```

<210> SEQ ID NO 6
<211> LENGTH: 419
<212> TYPE: PRT
<213> ORGANISM: Homo sapiens

<400> SEQUENCE: 6

```
Ala Asn Ser Phe Leu Glu Glu Leu Arg His Ser Ser Leu Glu Arg Glu
  1               5                  10                  15

Cys Ile Glu Glu Ile Cys Asp Phe Glu Ala Lys Glu Ile Phe Gln
                 20                  25                  30

Asn Val Asp Asp Thr Leu Ala Phe Trp Ser Lys His Val Asp Gly Asp
             35                  40                  45

Gln Cys Leu Val Leu Pro Leu Glu His Pro Cys Ala Ser Leu Cys Cys
         50                  55                  60

Gly His Gly Thr Cys Ile Asp Gly Ile Gly Ser Phe Ser Cys Asp Cys
 65                  70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
```

```
                    370                 375                 380
Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 7
<211> LENGTH: 419
<212> TYPE: PRT
<213> ORGANISM: Homo sapiens

<400> SEQUENCE: 7

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
```

```
                    325                 330                 335
Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
                355                 360                 365

His Gly Thr Trp Phe Leu Val Gly Leu Val Ser Trp Gly Glu Gly Cys
        370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                    405                 410                 415

Trp Ala Pro

<210> SEQ ID NO 8
<211> LENGTH: 419
<212> TYPE: PRT
<213> ORGANISM: Homo sapiens

<400> SEQUENCE: 8

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
                20                  25                  30

Asn Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
        210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
```

```
              275                 280                 285
Asn Gln Ala Gly Gln Glu Thr Leu Val Thr Gly Trp Gly Tyr His Ser
 290                 295                 300

Ser Arg Glu Lys Glu Ala Lys Arg Asn Arg Thr Phe Val Leu Asn Phe
305                 310                 315                 320

Ile Lys Ile Pro Val Pro His Asn Glu Cys Ser Glu Val Met Ser
                325                 330                 335

Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
                355                 360                 365

His Gly Thr Trp Phe Leu Val Gly Leu Val Ser Trp Gly Glu Gly Cys
        370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 9
<211> LENGTH: 419
<212> TYPE: PRT
<213> ORGANISM: Homo sapiens

<400> SEQUENCE: 9

Ala Asn Ser Phe Leu Glu Glu Leu Arg His Ser Ser Leu Glu Arg Glu
 1               5                  10                  15

Cys Ile Glu Glu Ile Cys Asp Phe Glu Glu Ala Lys Glu Ile Phe Gln
                20                  25                  30

Asn Val Asp Asp Thr Leu Ala Phe Trp Ser Lys His Val Asp Gly Asp
                35                  40                  45

Gln Cys Leu Val Leu Pro Leu Glu His Pro Cys Ala Ser Leu Cys Cys
     50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
                100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
                180                 185                 190

Lys Leu Ala Cys Gly Ala Val Leu Ile His Pro Ser Trp Val Leu Thr
        195                 200                 205

Ala Ala His Arg Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
```

```
                225                 230                 235                 240
Lys Glu Val Phe Val His Pro Asn Tyr Ser Lys Ser Thr Thr Asp Asn
                    245                 250                 255

Asp Ile Ala Leu Leu His Leu Ala Gln Pro Ala Thr Leu Ser Gln Thr
                260                 265                 270

Ile Val Pro Ile Cys Leu Pro Asp Ser Gly Leu Ala Glu Arg Glu Leu
            275                 280                 285

Asn Gln Ala Gly Gln Glu Thr Leu Val Thr Gly Trp Gly Tyr His Ser
        290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
        370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 10
<211> LENGTH: 419
<212> TYPE: PRT
<213> ORGANISM: Homo sapiens

<400> SEQUENCE: 10

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
```

```
                    180                 185                 190
Lys Leu Ala Cys Gly Ala Val Leu Ile His Pro Ser Trp Val Leu Thr
                195                 200                 205

Ala Ala His Arg Met Asp Glu Ser Lys Lys Leu Leu Val Arg Leu Gly
            210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
275                 280                 285

Asn Gln Ala Gly Gln Glu Thr Leu Val Thr Gly Trp Gly Tyr His Ser
            290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 11
<211> LENGTH: 419
<212> TYPE: PRT
<213> ORGANISM: Homo sapiens

<400> SEQUENCE: 11

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
```

```
                    130                 135                 140
Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                    165                 170                 175

Arg Arg Gly Asp Ser Pro Trp Gln Val Val Leu Leu Asp Ser Lys Lys
                180                 185                 190

Lys Leu Ala Cys Gly Ala Val Leu Ile His Pro Ser Trp Val Leu Thr
                195                 200                 205

Ala Ala His Cys Met Asp Glu Ser Lys Lys Leu Leu Val Arg Leu Gly
                210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
                    245                 250                 255

Asp Ile Ala Leu Leu His Leu Ala Gln Pro Ala Thr Leu Ser Gln Thr
                260                 265                 270

Ile Val Pro Ile Cys Leu Pro Asp Ser Gly Leu Ala Glu Arg Glu Leu
                275                 280                 285

Asn Gln Ala Gly Gln Glu Thr Leu Val Thr Gly Trp Gly Tyr His Ser
290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                    325                 330                 335

Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
                355                 360                 365

His Gly Thr Trp Phe Leu Val Gly Leu Val Ser Trp Gly Glu Gly Cys
                370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                    405                 410                 415

Trp Ala Pro

<210> SEQ ID NO 12
<211> LENGTH: 419
<212> TYPE: PRT
<213> ORGANISM: Homo sapiens

<400> SEQUENCE: 12

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
                20                  25                  30

Asn Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
        50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
```

```
            85                  90                  95
Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
            130                 135                 140

Trp Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
            165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
            195                 200                 205

Ala Ala His Arg Met Asp Glu Ser Lys Lys Leu Leu Val Arg Leu Gly
            210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
            245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
            275                 280                 285

Asn Gln Ala Gly Gln Glu Thr Leu Val Thr Gly Trp Gly Tyr His Ser
            290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
            325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
            370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
            405                 410                 415

Trp Ala Pro

<210> SEQ ID NO 13
<211> LENGTH: 419
<212> TYPE: PRT
<213> ORGANISM: Homo sapiens

<400> SEQUENCE: 13

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
```

```
              35                  40                  45
Gln Cys Leu Val Leu Pro Leu Glu His Pro Cys Ala Ser Leu Cys Cys
 50                  55                  60

Gly His Gly Thr Cys Ile Asp Gly Ile Gly Ser Phe Ser Cys Asp Cys
 65                  70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
                100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
    130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 14
<211> LENGTH: 419
<212> TYPE: PRT
<213> ORGANISM: Homo sapiens
```

<400> SEQUENCE: 14

```
Ala Asn Ser Phe Leu Glu Glu Leu Arg His Ser Ser Leu Glu Arg Glu
 1               5                  10                  15
Cys Ile Glu Glu Ile Cys Asp Phe Glu Glu Ala Lys Glu Ile Phe Gln
             20                  25                  30
Asn Val Asp Asp Thr Leu Ala Phe Trp Ser Lys His Val Asp Gly Asp
         35                  40                  45
Gln Cys Leu Val Leu Pro Leu Glu His Pro Cys Ala Ser Leu Cys Cys
     50                  55                  60
Gly His Gly Thr Cys Ile Asp Gly Ile Gly Ser Phe Ser Cys Asp Cys
 65                  70                  75                  80
Arg Ser Gly Trp Glu Gly Arg Phe Cys Gln Arg Glu Val Ser Phe Leu
                 85                  90                  95
Asn Cys Ser Leu Asp Asn Gly Gly Cys Thr His Tyr Cys Leu Glu Glu
            100                 105                 110
Val Gly Trp Arg Arg Cys Ser Cys Ala Pro Gly Tyr Lys Leu Gly Asp
        115                 120                 125
Asp Leu Leu Gln Cys His Pro Ala Val Lys Phe Pro Cys Gly Arg Pro
    130                 135                 140
Trp Lys Arg Met Glu Lys Lys Arg Ser His Leu Lys Arg Asp Thr Glu
145                 150                 155                 160
Asp Gln Glu Asp Gln Val Asp Pro Arg Leu Ile Asp Gly Lys Met Thr
                165                 170                 175
Gly Arg Gly Asp Ser Pro Trp Gln Val Val Leu Leu Asp Ser Lys Lys
            180                 185                 190
Lys Leu Ala Cys Gly Ala Val Leu Ile His Pro Ser Trp Val Leu Thr
        195                 200                 205
Ala Ala His Cys Met Asp Glu Ser Lys Lys Leu Leu Val Arg Leu Gly
    210                 215                 220
Glu Tyr Asp Leu Ala Ala Trp Glu Lys Trp Glu Leu Asp Leu Asp Ile
225                 230                 235                 240
Lys Glu Val Phe Val His Pro Asn Tyr Ser Lys Ser Thr Thr Asp Asn
                245                 250                 255
Asp Ile Ala Leu Leu His Leu Ala Gln Pro Ala Thr Leu Ser Gln Thr
            260                 265                 270
Ile Val Pro Ile Cys Leu Pro Asp Ser Gly Leu Ala Glu Arg Glu Leu
        275                 280                 285
Asn Gln Ala Gly Gln Glu Thr Leu Val Thr Gly Trp Gly Tyr His Ser
    290                 295                 300
Ser Arg Glu Lys Glu Ala Lys Arg Asn Arg Thr Phe Val Leu Asn Phe
305                 310                 315                 320
Ile Lys Ile Pro Val Val Pro His Asn Glu Cys Ser Glu Val Met Ser
                325                 330                 335
Asn Met Val Ser Glu Asn Met Leu Cys Ala Gly Ile Leu Gly Asp Arg
            340                 345                 350
Gln Asp Ala Cys Glu Gly Asp Ser Gly Gly Pro Met Val Ala Ser Phe
        355                 360                 365
His Gly Thr Trp Phe Leu Val Gly Leu Val Ser Trp Gly Glu Gly Cys
    370                 375                 380
Gly Leu Leu His Asn Tyr Gly Val Tyr Thr Lys Val Ser Arg Tyr Leu
385                 390                 395                 400
Asp Trp Ile His Gly His Ile Arg Asp Lys Glu Ala Pro Gln Lys Ser
                405                 410                 415
```

Trp Ala Pro

<210> SEQ ID NO 15
<211> LENGTH: 419
<212> TYPE: PRT
<213> ORGANISM: Homo sapiens

<400> SEQUENCE: 15

```
Ala Asn Ser Phe Leu Glu Glu Leu Arg His Ser Ser Leu Glu Arg Glu
 1               5                  10                  15
Cys Ile Glu Glu Ile Cys Asp Phe Glu Glu Ala Lys Glu Ile Phe Gln
                20                  25                  30
Asn Val Asp Asp Thr Leu Ala Phe Trp Ser Lys His Val Asp Gly Asp
                35                  40                  45
Gln Cys Leu Val Leu Pro Leu Glu His Pro Cys Ala Ser Leu Cys Cys
        50                  55                  60
Gly His Gly Thr Cys Ile Asp Gly Ile Gly Ser Phe Ser Cys Asp Cys
65                  70                  75                  80
Arg Ser Gly Trp Glu Gly Arg Phe Cys Gln Arg Glu Val Ser Phe Leu
                85                  90                  95
Asn Cys Ser Leu Asp Asn Gly Gly Cys Thr His Tyr Cys Leu Glu Glu
                100                 105                 110
Val Gly Trp Arg Arg Cys Ser Cys Ala Pro Gly Tyr Lys Leu Gly Asp
                115                 120                 125
Asp Leu Leu Gln Cys His Pro Ala Val Lys Phe Pro Cys Gly Arg Pro
        130                 135                 140
Trp Gly Gly Met Glu Lys Lys Arg Ser His Leu Lys Arg Asp Thr Glu
145                 150                 155                 160
Asp Gln Glu Asp Gln Val Asp Pro Arg Leu Ile Asp Gly Lys Met Thr
                165                 170                 175
Gly Arg Gly Asp Ser Pro Trp Gln Val Val Leu Leu Asp Ser Lys Lys
                180                 185                 190
Lys Leu Ala Cys Gly Ala Val Leu Ile His Pro Ser Trp Val Leu Thr
                195                 200                 205
Ala Ala His Arg Met Asp Glu Ser Lys Lys Leu Leu Val Arg Leu Gly
        210                 215                 220
Glu Tyr Asp Leu Ala Ala Trp Glu Lys Trp Glu Leu Asp Leu Asp Ile
225                 230                 235                 240
Lys Glu Val Phe Val His Pro Asn Tyr Ser Lys Ser Thr Thr Asp Asn
                245                 250                 255
Asp Ile Ala Leu Leu His Leu Ala Gln Pro Ala Thr Leu Ser Gln Thr
                260                 265                 270
Ile Val Pro Ile Cys Leu Pro Asp Ser Gly Leu Ala Glu Arg Glu Leu
                275                 280                 285
Asn Gln Ala Gly Gln Glu Thr Leu Val Thr Gly Trp Gly Tyr His Ser
        290                 295                 300
Ser Arg Glu Lys Glu Ala Lys Arg Asn Arg Thr Phe Val Leu Asn Phe
305                 310                 315                 320
Ile Lys Ile Pro Val Val Pro His Asn Glu Cys Ser Glu Val Met Ser
                325                 330                 335
Asn Met Val Ser Glu Asn Met Leu Cys Ala Gly Ile Leu Gly Asp Arg
                340                 345                 350
Gln Asp Ala Cys Glu Gly Asp Ser Gly Gly Pro Met Val Ala Ser Phe
                355                 360                 365
```

His Gly Thr Trp Phe Leu Val Gly Leu Val Ser Trp Gly Glu Gly Cys
             370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 16
<211> LENGTH: 419
<212> TYPE: PRT
<213> ORGANISM: Homo sapiens

<400> SEQUENCE: 16

Ala Asn Ser Phe Leu Glu Glu Leu Arg His Ser Ser Leu Glu Arg Glu
  1               5                  10                  15

Cys Ile Glu Glu Ile Cys Asp Phe Glu Glu Ala Lys Glu Ile Phe Gln
             20                  25                  30

Asn Val Asp Asp Thr Leu Ala Phe Trp Ser Lys His Val Asp Gly Asp
             35                  40                  45

Gln Cys Leu Val Leu Pro Leu Glu His Pro Cys Ala Ser Leu Cys Cys
     50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
                100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Arg Met Asp Glu Ser Lys Lys Leu Leu Val Arg Leu Gly
210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
290                 295                 300

Ser Arg Glu Lys Glu Ala Lys Arg Asn Arg Thr Phe Val Leu Asn Phe
305                 310                 315                 320

```
Ile Lys Ile Pro Val Pro His Asn Glu Cys Ser Glu Val Met Ser
            325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
            405                 410                 415

Trp Ala Pro

<210> SEQ ID NO 17
<211> LENGTH: 419
<212> TYPE: PRT
<213> ORGANISM: Homo sapiens

<400> SEQUENCE: 17

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
            195                 200                 205

Ala Ala His Cys Met Asp Glu Ser Lys Lys Leu Leu Val Arg Leu Gly
210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270
```

```
Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
                355                 360                 365

His Gly Thr Trp Phe Leu Val Gly Leu Val Ser Trp Gly Glu Gly Cys
            370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 18
<211> LENGTH: 419
<212> TYPE: PRT
<213> ORGANISM: Homo sapiens

<400> SEQUENCE: 18

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
                20                  25                  30

Asn Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
210                 215                 220
```

```
Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
            245                 250                 255

Asp Ile Ala Leu Leu His Leu Ala Gln Pro Ala Thr Leu Ser Gln Thr
        260                 265                 270

Ile Val Pro Ile Cys Leu Pro Asp Ser Gly Leu Ala Glu Arg Glu Leu
    275                 280                 285

Asn Gln Ala Gly Gln Glu Thr Leu Val Thr Gly Trp Gly Tyr His Ser
290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 19
<211> LENGTH: 419
<212> TYPE: PRT
<213> ORGANISM: Homo sapiens

<400> SEQUENCE: 19

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175
```

```
Gly Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 20
<211> LENGTH: 419
<212> TYPE: PRT
<213> ORGANISM: Homo sapiens

<400> SEQUENCE: 20

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125
```

```
Asp Leu Leu Gln Cys His Pro Ala Val Lys Phe Pro Cys Gly Arg Pro
            130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Arg Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 21
<211> LENGTH: 419
<212> TYPE: PRT
<213> ORGANISM: Homo sapiens

<400> SEQUENCE: 21

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80
```

```
Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Arg Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 22
<211> LENGTH: 419
<212> TYPE: PRT
<213> ORGANISM: Homo sapiens

<400> SEQUENCE: 22

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30
```

```
Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
 50                  55                  60

Gly His Gly Thr Cys Ile Asp Gly Ile Gly Ser Phe Ser Cys Asp Cys
 65                  70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
                100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
        130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Arg Met Asp Glu Ser Lys Lys Leu Leu Val Arg Leu Gly
        210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
        290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
        370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 23
<211> LENGTH: 419
<212> TYPE: PRT
```

<213> ORGANISM: Homo sapiens

<400> SEQUENCE: 23

```
Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400
```

-continued

Asp Trp Ile His Gly His Ile Arg Asp Lys Glu Ala Pro Gln Lys Ser
            405                 410                 415

Trp Ala Pro

<210> SEQ ID NO 24
<211> LENGTH: 419
<212> TYPE: PRT
<213> ORGANISM: Homo sapiens

<400> SEQUENCE: 24

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

```
Gln Asp Ala Cys Glu Gly Asp Ser Gly Gly Pro Met Val Ala Ser Phe
            355                 360                 365
His Gly Thr Trp Phe Leu Val Gly Leu Val Ser Trp Gly Glu Gly Cys
    370                 375                 380
Gly Leu Leu His Asn Tyr Gly Val Tyr Thr Lys Val Ser Arg Tyr Leu
385                 390                 395                 400
Asp Trp Ile His Gly His Ile Arg Asp Lys Glu Ala Pro Gln Lys Ser
                405                 410                 415
Trp Ala Pro

<210> SEQ ID NO 25
<211> LENGTH: 419
<212> TYPE: PRT
<213> ORGANISM: Homo sapiens

<400> SEQUENCE: 25

Ala Asn Ser Phe Leu Glu Glu Leu Arg His Ser Ser Leu Glu Arg Glu
1               5                   10                  15
Cys Ile Glu Glu Ile Cys Asp Phe Glu Glu Ala Lys Glu Ile Phe Gln
            20                  25                  30
Asn Val Asp Asp Thr Leu Ala Phe Trp Ser Lys His Val Asp Gly Asp
        35                  40                  45
Gln Cys Leu Val Leu Pro Leu Glu His Pro Cys Ala Ser Leu Cys Cys
    50                  55                  60
Gly His Gly Thr Cys Ile Asp Gly Ile Gly Ser Phe Ser Cys Asp Cys
65                  70                  75                  80
Arg Ser Gly Trp Glu Gly Arg Phe Cys Gln Arg Glu Val Ser Phe Leu
                85                  90                  95
Asn Cys Ser Leu Asp Asn Gly Gly Cys Thr His Tyr Cys Leu Glu Glu
            100                 105                 110
Val Gly Trp Arg Arg Cys Ser Cys Ala Pro Gly Tyr Lys Leu Gly Asp
        115                 120                 125
Asp Leu Leu Gln Cys His Pro Ala Val Lys Phe Pro Cys Gly Arg Pro
    130                 135                 140
Trp Gly Gly Met Glu Lys Lys Arg Ser His Leu Lys Arg Asp Thr Glu
145                 150                 155                 160
Asp Gln Glu Asp Gln Val Asp Pro Arg Leu Ile Asp Gly Lys Met Thr
                165                 170                 175
Gly Arg Gly Asp Ser Pro Trp Gln Val Val Leu Leu Asp Ser Ala Ala
            180                 185                 190
Ala Leu Ala Cys Gly Ala Val Leu Ile His Pro Ser Trp Val Leu Thr
        195                 200                 205
Ala Ala His Cys Met Asp Glu Ser Lys Lys Leu Leu Val Arg Leu Gly
    210                 215                 220
Glu Tyr Asp Leu Ala Ala Trp Glu Lys Trp Glu Leu Asp Leu Asp Ile
225                 230                 235                 240
Lys Glu Val Phe Val His Pro Asn Tyr Ser Lys Ser Thr Thr Asp Asn
                245                 250                 255
Asp Ile Ala Leu Leu His Leu Ala Gln Pro Ala Thr Leu Ser Gln Thr
            260                 265                 270
Ile Val Pro Ile Cys Leu Pro Asp Ser Gly Leu Ala Glu Arg Glu Leu
        275                 280                 285
Asn Gln Ala Gly Gln Glu Thr Leu Val Thr Gly Trp Gly Tyr His Ser
    290                 295                 300
```

```
Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
                355                 360                 365

His Gly Thr Trp Phe Leu Val Gly Leu Val Ser Trp Gly Glu Gly Cys
370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 26
<211> LENGTH: 419
<212> TYPE: PRT
<213> ORGANISM: Homo sapiens

<400> SEQUENCE: 26

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
                20                  25                  30

Asn Val Asp Asp Thr Leu Ala Phe Trp Ser Lys His Val Asp Gly Asp
                35                  40                  45

Gln Cys Leu Val Leu Pro Leu Glu His Pro Cys Ala Ser Leu Cys Cys
            50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
                100                 105                 110

Val Gly Trp Arg Arg Cys Ser Cys Ala Pro Gly Tyr Lys Leu Gly Asp
                115                 120                 125

Asp Leu Leu Gln Cys His Pro Ala Val Lys Phe Pro Cys Gly Arg Pro
130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Ala Ala
                180                 185                 190

Ala Leu Ala Cys Gly Ala Val Leu Ile His Pro Ser Trp Val Leu Thr
            195                 200                 205

Ala Ala His Arg Met Asp Glu Ser Lys Lys Leu Leu Val Arg Leu Gly
210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255
```

```
Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 27
<211> LENGTH: 419
<212> TYPE: PRT
<213> ORGANISM: Homo sapiens

<400> SEQUENCE: 27

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205
```

-continued

```
Ala Ala His Arg Met Asp Glu Ser Lys Lys Leu Leu Val Arg Leu Gly
    210                 215                 220
Glu Tyr Asp Leu Ala Ala Trp Glu Lys Trp Glu Leu Asp Leu Asp Ile
225                 230                 235                 240
Lys Glu Val Phe Val His Pro Asn Tyr Ser Lys Ser Thr Thr Asp Asn
                245                 250                 255
Asp Ile Ala Leu Leu His Leu Ala Gln Pro Ala Thr Leu Ser Gln Thr
            260                 265                 270
Ile Val Pro Ile Cys Leu Pro Asp Ser Gly Leu Ala Glu Arg Glu Leu
        275                 280                 285
Asn Gln Ala Gly Gln Glu Thr Leu Val Thr Gly Trp Gly Tyr His Ser
    290                 295                 300
Ser Arg Glu Lys Glu Ala Lys Arg Asn Arg Thr Phe Val Leu Asn Phe
305                 310                 315                 320
Ile Lys Ile Pro Val Val Pro His Asn Glu Cys Ser Glu Val Met Ser
                325                 330                 335
Asn Met Val Ser Glu Asn Met Leu Cys Ala Gly Ile Leu Gly Asp Arg
            340                 345                 350
Gln Asp Ala Cys Glu Gly Asp Ser Gly Gly Pro Met Val Ala Ser Phe
        355                 360                 365
His Gly Thr Trp Phe Leu Val Gly Leu Val Ser Trp Gly Glu Gly Cys
    370                 375                 380
Gly Leu Leu His Asn Tyr Gly Val Tyr Thr Lys Val Ser Arg Tyr Leu
385                 390                 395                 400
Asp Trp Ile His Gly His Ile Arg Asp Lys Glu Ala Pro Gln Lys Ser
                405                 410                 415
Trp Ala Pro

<210> SEQ ID NO 28
<211> LENGTH: 419
<212> TYPE: PRT
<213> ORGANISM: Homo sapiens

<400> SEQUENCE: 28

Ala Asn Ser Phe Leu Glu Glu Leu Arg His Ser Ser Leu Glu Arg Glu
1               5                   10                  15
Cys Ile Glu Glu Ile Cys Asp Phe Glu Glu Ala Lys Glu Ile Phe Gln
            20                  25                  30
Asn Val Asp Asp Thr Leu Ala Phe Trp Ser Lys His Val Asp Gly Asp
        35                  40                  45
Gln Cys Leu Val Leu Pro Leu Glu His Pro Cys Ala Ser Leu Cys Cys
    50                  55                  60
Gly His Gly Thr Cys Ile Asp Gly Ile Gly Ser Phe Ser Cys Asp Cys
65                  70                  75                  80
Arg Ser Gly Trp Glu Gly Arg Phe Cys Gln Arg Glu Val Ser Phe Leu
                85                  90                  95
Asn Cys Ser Leu Asp Asn Gly Gly Cys Thr His Tyr Cys Leu Glu Glu
            100                 105                 110
Val Gly Trp Arg Arg Cys Ser Cys Ala Pro Gly Tyr Lys Leu Gly Asp
        115                 120                 125
Asp Leu Leu Gln Cys His Pro Ala Val Lys Phe Pro Cys Gly Arg Pro
    130                 135                 140
Trp Gly Gly Met Glu Lys Lys Arg Ser His Leu Lys Arg Asp Thr Glu
145                 150                 155                 160
```

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Arg Met Asp Glu Ser Lys Lys Leu Leu Val Arg Leu Gly
    210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 29
<211> LENGTH: 419
<212> TYPE: PRT
<213> ORGANISM: Homo sapiens

<400> SEQUENCE: 29

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
                195                 200                 205

Ala Ala His Arg Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
    275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
    355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 30
<211> LENGTH: 419
<212> TYPE: PRT
<213> ORGANISM: Homo sapiens

<400> SEQUENCE: 30

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

```
Gly His Gly Thr Cys Ile Asp Gly Ile Gly Ser Phe Ser Cys Asp Cys
 65                  70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Gly Gly Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Arg Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 31
<211> LENGTH: 419
<212> TYPE: PRT
<213> ORGANISM: Homo sapiens

<400> SEQUENCE: 31

Ala Asn Ser Phe Leu Glu Glu Leu Arg His Ser Ser Leu Glu Arg Glu
 1               5                  10                  15
```

```
Cys Ile Glu Glu Ile Cys Asp Phe Glu Ala Lys Glu Ile Phe Gln
             20                  25                  30

Asn Val Asp Asp Thr Leu Ala Phe Trp Ser Lys His Val Asp Gly Asp
             35                  40                  45

Gln Cys Leu Val Leu Pro Leu Glu His Pro Cys Ala Ser Leu Cys Cys
 50                  55                  60

Gly His Gly Thr Cys Ile Asp Gly Ile Gly Ser Phe Ser Cys Asp Cys
 65                  70                  75                  80

Arg Ser Gly Trp Glu Gly Arg Phe Cys Gln Arg Glu Val Ser Phe Leu
                 85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
            130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
            195                 200                 205

Ala Ala His Arg Met Asp Glu Ser Lys Lys Leu Leu Val Arg Leu Gly
210                 215                 220

Glu Tyr Asp Leu Ala Ala Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
            275                 280                 285

Asn Gln Ala Gly Gln Glu Thr Leu Val Thr Gly Trp Gly Tyr His Ser
290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
            370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 32
```

<211> LENGTH: 419
<212> TYPE: PRT
<213> ORGANISM: Homo sapiens

<400> SEQUENCE: 32

```
Ala Asn Ser Phe Leu Glu Glu Leu Arg His Ser Ser Leu Glu Arg Glu
 1               5                  10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Gly Arg Gly Asp Ser Pro Trp Gln Val Val Leu Leu Asp Ser Ala Ala
            180                 185                 190

Ala Leu Ala Cys Gly Ala Val Leu Ile His Pro Ser Trp Val Leu Thr
        195                 200                 205

Ala Ala His Arg Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
```

```
385                 390                 395                 400
Asp Trp Ile His Gly His Ile Arg Asp Lys Glu Ala Pro Gln Lys Ser
                    405                 410                 415

Trp Ala Pro

<210> SEQ ID NO 33
<211> LENGTH: 31
<212> TYPE: DNA
<213> ORGANISM: Artificial Sequence
<220> FEATURE:
<223> OTHER INFORMATION: Oligonucleotide

<400> SEQUENCE: 33
gaccaggcgg ggagagagcc cctggcaggt g                                    31

<210> SEQ ID NO 34
<211> LENGTH: 31
<212> TYPE: DNA
<213> ORGANISM: Artificial Sequence
<220> FEATURE:
<223> OTHER INFORMATION: Oligonucleotide

<400> SEQUENCE: 34
cacctgccag gggctctctc cccgcctggt c                                    31

<210> SEQ ID NO 35
<211> LENGTH: 37
<212> TYPE: DNA
<213> ORGANISM: Artificial Sequence
<220> FEATURE:
<223> OTHER INFORMATION: Oligonucleotide

<400> SEQUENCE: 35
atataaagct tgccaccatg ttgacaacat tgctgcc                              37

<210> SEQ ID NO 36
<211> LENGTH: 33
<212> TYPE: DNA
<213> ORGANISM: Artificial Sequence
<220> FEATURE:
<223> OTHER INFORMATION: Oligonucleotide

<400> SEQUENCE: 36 tataccgg tccacatcgc cgtccacctg tgc                                    33

<210> SEQ ID NO 37
<211> LENGTH: 37
<212> TYPE: DNA
<213> ORGANISM: Artificial Sequence
<220> FEATURE:
<223> OTHER INFORMATION: Oligonucleotide

<400> SEQUENCE: 37
atatactcga ggccaccatg aatttacaac caattt                               37

<210> SEQ ID NO 38
<211> LENGTH: 33
<212> TYPE: DNA
<213> ORGANISM: Artificial Sequence
<220> FEATURE:
<223> OTHER INFORMATION: Oligonucleotide

<400> SEQUENCE: 38 tataccgg tccttttccc tcatacttcg gat                                    33
```

```
<210> SEQ ID NO 39
<211> LENGTH: 14
<212> TYPE: PRT
<213> ORGANISM: Aritficial Sequence
<220> FEATURE:
<223> OTHER INFORMATION: Sequence synthesized

<400> SEQUENCE: 39

Ser Phe Leu Leu Arg Asn Pro Asn Asp Lys Tyr Glu Pro Phe
 1               5                  10

<210> SEQ ID NO 40
<211> LENGTH: 12
<212> TYPE: PRT
<213> ORGANISM: Homo sapiens

<400> SEQUENCE: 40

Tyr Ala Val Thr Gly Arg Gly Asp Ser Pro Ala Ser
 1               5                  10

<210> SEQ ID NO 41
<211> LENGTH: 12
<212> TYPE: PRT
<213> ORGANISM: Homo sapiens

<400> SEQUENCE: 41

Gly Lys Met Thr Arg Arg Gly Asp Ser Pro Trp Gln
 1               5                  10

<210> SEQ ID NO 42
<211> LENGTH: 419
<212> TYPE: PRT
<213> ORGANISM: Homo sapiens

<400> SEQUENCE: 42

Ala Asn Ser Phe Leu Glu Glu Leu Arg His Ser Ser Leu Glu Arg Glu
 1               5                  10                  15

Cys Ile Glu Glu Ile Cys Asp Phe Glu Glu Ala Lys Glu Ile Phe Gln
                20                  25                  30

Asn Val Asp Asp Thr Leu Ala Phe Trp Ser Lys His Val Asp Gly Asp
            35                  40                  45

Gln Cys Leu Val Leu Pro Leu Glu His Pro Cys Ala Ser Leu Cys Cys
        50                  55                  60

Gly His Gly Thr Cys Ile Asp Gly Ile Gly Ser Phe Ser Cys Asp Cys
    65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
                100                 105                 110

Val Gly Trp Arg Arg Cys Ser Cys Ala Pro Gly Tyr Lys Leu Gly Asp
            115                 120                 125

Asp Leu Leu Gln Cys His Pro Ala Val Lys Phe Pro Cys Gly Arg Pro
        130                 135                 140

Trp Arg Arg Met Glu Lys Lys Arg Ser His Leu Lys Arg Asp Thr Glu
    145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190
```

```
Lys Leu Ala Cys Gly Ala Val Leu Ile His Pro Ser Trp Val Leu Thr
            195                 200                 205

Ala Ala His Cys Met Asp Glu Ser Lys Lys Leu Leu Val Arg Leu Gly
        210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro

<210> SEQ ID NO 43
<211> LENGTH: 419
<212> TYPE: PRT
<213> ORGANISM: Homo sapiens

<400> SEQUENCE: 43

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140
```

-continued

| | | | | | | | | | | | | | | | |
|---|---|---|---|---|---|---|---|---|---|---|---|---|---|---|---|
| Trp | Lys | Arg | Met | Glu | Lys | Arg | Ser | His | Leu | Lys | Arg | Asp | Thr | Glu |
| 145 | | | | 150 | | | | 155 | | | | | | 160 |
| Asp | Gln | Glu | Asp | Gln | Val | Asp | Pro | Arg | Leu | Ile | Asn | Gly | Lys | Met | Thr |
| | | | | 165 | | | | | 170 | | | | | 175 | |
| Arg | Arg | Gly | Asp | Ser | Pro | Trp | Gln | Val | Val | Leu | Leu | Asp | Ser | Lys | Lys |
| | | | 180 | | | | | 185 | | | | | 190 | | |
| Lys | Leu | Ala | Cys | Gly | Ala | Val | Leu | Ile | His | Pro | Ser | Trp | Val | Leu | Thr |
| | | 195 | | | | | 200 | | | | | 205 | | | |
| Ala | Ala | His | Cys | Met | Asp | Glu | Ser | Lys | Lys | Leu | Leu | Val | Arg | Leu | Gly |
| | 210 | | | | | 215 | | | | | 220 | | | | |
| Glu | Tyr | Asp | Leu | Arg | Arg | Trp | Glu | Lys | Trp | Glu | Leu | Asp | Leu | Asp | Ile |
| 225 | | | | | 230 | | | | | 235 | | | | | 240 |
| Lys | Glu | Val | Phe | Val | His | Pro | Asn | Tyr | Ser | Lys | Ser | Thr | Thr | Asp | Asn |
| | | | | 245 | | | | | 250 | | | | | 255 | |
| Asp | Ile | Ala | Leu | Leu | His | Leu | Ala | Gln | Pro | Ala | Thr | Leu | Ser | Gln | Thr |
| | | | | 260 | | | | | 265 | | | | | 270 | |
| Ile | Val | Pro | Ile | Cys | Leu | Pro | Asp | Ser | Gly | Leu | Ala | Glu | Arg | Glu | Leu |
| | | | 275 | | | | | 280 | | | | | 285 | | |
| Asn | Gln | Ala | Gly | Gln | Glu | Thr | Leu | Val | Thr | Gly | Trp | Gly | Tyr | His | Ser |
| | | 290 | | | | | 295 | | | | | 300 | | | |
| Ser | Arg | Glu | Lys | Glu | Ala | Lys | Arg | Asn | Arg | Thr | Phe | Val | Leu | Asn | Phe |
| 305 | | | | | 310 | | | | | 315 | | | | | 320 |
| Ile | Lys | Ile | Pro | Val | Val | Pro | His | Asn | Glu | Cys | Ser | Glu | Val | Met | Ser |
| | | | | 325 | | | | | 330 | | | | | 335 | |
| Asn | Met | Val | Ser | Glu | Asn | Met | Leu | Cys | Ala | Gly | Ile | Leu | Gly | Asp | Arg |
| | | | 340 | | | | | 345 | | | | | 350 | | |
| Gln | Asp | Ala | Cys | Glu | Gly | Asp | Ser | Gly | Gly | Pro | Met | Val | Ala | Ser | Phe |
| | | | 355 | | | | | 360 | | | | | 365 | | |
| His | Gly | Thr | Trp | Phe | Leu | Val | Gly | Leu | Val | Ser | Trp | Gly | Glu | Gly | Cys |
| | 370 | | | | | 375 | | | | | 380 | | | | |
| Gly | Leu | Leu | His | Asn | Tyr | Gly | Val | Tyr | Thr | Lys | Val | Ser | Arg | Tyr | Leu |
| 385 | | | | | 390 | | | | | 395 | | | | | 400 |
| Asp | Trp | Ile | His | Gly | His | Ile | Arg | Asp | Lys | Glu | Ala | Pro | Gln | Lys | Ser |
| | | | | 405 | | | | | 410 | | | | | 415 | |
| Trp | Ala | Pro | | | | | | | | | | | | | |